United States Patent
Shiratani et al.

(10) Patent No.: US 9,796,831 B2
(45) Date of Patent: Oct. 24, 2017

(54) PROCESS FOR PRODUCING PARTICLES

(75) Inventors: Hiroshi Shiratani, Osaka (JP);
Masahito Sekiguchi, Osaka (JP);
Yasuo Uekita, Osaka (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 992 days.

(21) Appl. No.: 14/114,682

(22) PCT Filed: Apr. 24, 2012

(86) PCT No.: PCT/JP2012/061515
§ 371 (c)(1),
(2), (4) Date: Oct. 29, 2013

(87) PCT Pub. No.: WO2012/153672
PCT Pub. Date: Nov. 15, 2012

(65) Prior Publication Data
US 2014/0065337 A1  Mar. 6, 2014

(30) Foreign Application Priority Data

May 12, 2011  (JP) .................................. 2011-106947
May 12, 2011  (JP) .................................. 2011-106948

(51) Int. Cl.
*C08K 3/34* (2006.01)
*C08K 5/41* (2006.01)
*C07C 381/02* (2006.01)

(52) U.S. Cl.
CPC .............. *C08K 5/41* (2013.01); *C07C 381/02* (2013.01); *Y10T 428/1386* (2015.01); *Y10T 428/24479* (2015.01); *Y10T 428/296* (2015.01)

(58) Field of Classification Search
CPC ....................................................... C08K 5/41
USPC ....................................................... 524/445
See application file for complete search history.

(56) References Cited

U.S. PATENT DOCUMENTS

| | | | |
|---|---|---|---|
| 4,581,297 A | 4/1986 | Delseth et al. | |
| 5,106,913 A | 4/1992 | Yamaguchi et al. | |
| 5,256,362 A | 10/1993 | Goto et al. | |
| 6,211,278 B1 | 4/2001 | Vanel | |
| 7,560,218 B2 * | 7/2009 | Omatsu | G03G 9/0819 430/108.7 |
| 2009/0000721 A1 | 1/2009 | Imoto et al. | |
| 2012/0088928 A1 | 4/2012 | Ozturk et al. | |
| 2012/0101219 A1 * | 4/2012 | Ozturk | B60C 1/00 524/575.5 |
| 2013/0210978 A1 | 8/2013 | Uekita et al. | |

FOREIGN PATENT DOCUMENTS

| | | |
|---|---|---|
| EP | 1172406 A3 | 1/2002 |
| EP | 2439237 A1 | 4/2012 |
| JP | 60-199643 A | 10/1985 |
| JP | 03-163054 A | 7/1991 |
| JP | 2011-046857 A | 3/2011 |
| JP | 2011-046858 A | 3/2011 |
| JP | 2012-107232 A | 6/2012 |
| JP | 2012-144598 A | 8/2012 |
| RU | 2214427 C2 | 10/2003 |
| RU | 2394692 C2 | 7/2010 |

OTHER PUBLICATIONS

Extended European Search Report issued Jan. 5, 2015 in European Patent Application No. 12781691.6.
International Preliminary Report on Patentability and Written Opinion issued Nov. 21, 2013 in International Patent Application No. PCT/JP2012/061515.

* cited by examiner

*Primary Examiner* — Hui Chin
(74) *Attorney, Agent, or Firm* — Sughrue Mion, PLLC

(57) ABSTRACT

A process for producing particles, the process including pulverizing particles of a compound represented by formula (I) with a median diameter (50% D) of over 100 μm by using a pulverizer in the presence of at least one member selected from the group consisting of silica, talc and clay, to obtain particles of the compound represented by formula (I) with a median diameter (50% D) of 100 μm or less,

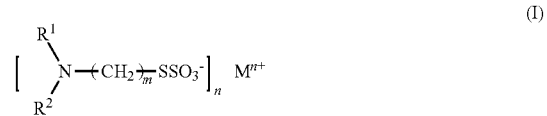

(I)

in formula (I), $R^1$ and $R^2$ each independently represent a hydrogen atom or an alkyl group having 1 to 6 carbon atoms, or alternatively, $R^1$ and $R^2$ are inked to each other to form a ring together with the nitrogen atom to which they are bound, m represents an integer of 2 to 9, $M^{n+}$ represents $H^+$ or an n-valent metal ion, and n represents an integer of 1 or 2.

7 Claims, No Drawings

PROCESS FOR PRODUCING PARTICLES

CROSS REFERENCE TO RELATED APPLICATIONS

This application is a National Stage of International Application No. PCT/JP2012/061515 filed Apr. 24, 2012, claiming priority based on Japanese Patent Application No. 2011-106947 filed May 12, 2011, and Japanese Patent Application No. 2011-106948 filed May 12, 2011, the contents of all of which are incorporated herein by reference in their entirety.

TECHNICAL FIELD

The present invention relates to a process for producing particles and the like.

BACKGROUND ART

WO 2011/001990 describes a compound represented by formula (I-1) as a compound contained in vulcanized rubber for tire.

DISCLOSURE OF THE INVENTION

The present invention includes the following inventions.

[1] A process for producing particles, the process comprising of pulverizing particles of a compound represented by formula (I) with a median diameter (50% D) of over 100 μm by using a pulverizer in the presence of at least one member selected from the group consisting of silica, talc and clay, to obtain particles of the compound represented by formula (I) with a median diameter (50% D) of 100 μm or less,

in formula (I), $R^1$ and $R^2$ each independently represent a hydrogen atom or an alkyl group having 1 to 6 carbon atoms, or alternatively, $R^1$ and $R^2$ are linked to each other to form a ring together with the nitrogen atom to which they are bound, m represents an integer of 2 to 9,
$M^{n+}$ represents $H^+$ or an n-valent metal ion and
n represents an integer of 1 or 2.

[2] The process according to [1], wherein the compound represented by formula (I) is a compound represented by formula (I-1):

[3] The process according to [1], wherein the pulverization is performed in the present of at least one member selected from the group consisting of silica, talc and clay in an amount of 0.1 to 9 parts by mass with respect to 1 part by mass of the compound represented by formula (I).

[4] The process according to any one of [1] to [3], wherein particles of a compound represented by formula (I) with a median diameter (50% D) of less than 10 μm are obtained.

[5] The process according to any one of [1] to [4], wherein the pulverizer is a jet mill or a bead mill.

[6] The process according to any one of [1] to [5], wherein the particles of a compound represented by formula (I) with a median diameter (50% D) of 100 μm or less are particles of a compound represented by formula (I) with a 95% particle diameter (95% D) of 50 μm or less.

[7] A process for producing vulcanized rubber, the process comprising a step (A) of kneading particles obtained by the process according to any one of [1] to [6], a rubber component and a filler together, step (B) of kneading the kneaded mixture obtained in the step (A), a sulfur component and a vulcanization accelerator, and step (C) of thermally treating the kneaded mixture obtained in the step (B).

[8] A composition comprising particles of a compound represented by formula (I) with a median diameter (50% D) of 100 μm or less and particles of at least one member selected from the group consisting of silica, talc and clay with a median diameter (50% D) of 100 μm or less:

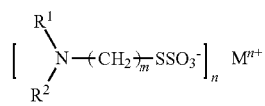

in formula (I), $R^1$ and $R^2$ each independently represent a hydrogen atom or an alkyl group having 1 to 6 carbon atoms, or alternatively, $R^1$ and $R^2$ are linked to each other to form a ring together with the nitrogen atom to which they are bound, m represents an integer of 2 to 9,
$M^{n+}$ represents $H^+$ or an n-valent metal ion, and
n represents an integer of 1 or 2.

[9] The composition according to [8], wherein the compound represented by formula (I) is a compound represented by formula (I-1):

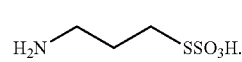

[10] The composition according to [8] or [9] comprising particles of a compound represented by formula (I) and particles of at least one member selected from the group consisting of silica, talc and clay, wherein a mixture of the particles of a compound represented by formula (I) and the particles of at least one member selected from the group consisting of silica, talc and clay has a median diameter (50% D) of 100 μm or less.

[11] The composition according to any one of [8] to [10] comprising at least one member selected from the group consisting of silica, talc and clay in an amount of 0.1 to 9 parts by mass with respect to 1 part by mass of the compound represented by formula (I).

[12] The composition according to any one of [8] to [11] comprising particles of a compound represented by formula (I) with a median diameter (50% D) of less than 10 μm and particles of at least one member selected from the group consisting of silica, talc and clay with a median diameter (50% D) of less than 10 μm.

[13] The composition according to any one of [8] to [12], wherein the pulverizer is a jet mill or a bead mill.

[14] The composition according to any one of [8] to [13], wherein the particles of a compound represented by formula (I) with a median diameter (50% D) of 100 μm or less are particles of a compound represented by formula (I) with a 95% particle diameter (95% D) of 50 μm or less.

[15] A rubber composition obtained by kneading the composition according to any one of [8] to [14], a rubber component, a filler, a sulfur component and a vulcanization accelerator.

[16] A vulcanized rubber obtained by thermally treating the rubber composition according to [15].

[17] A pneumatic tire produced by processing the rubber composition according to [15].

[18] A tire belt comprising a steel cord coated with the vulcanized rubber according to [16].

[19] A tire carcass containing a carcass fiber cord coated with the vulcanized rubber according to [16].

[20] A tire side wall, a tire inner liner, a tire cap tread or a tire under tread comprising the vulcanized rubber according to [16].

[21] A pneumatic tire comprising the vulcanized rubber according to [16].

MODES FOR CARRYING OUT THE INVENTION

The pulverizer includes a jet mill, a hammer mill, a bead mill, a turbo mill and the like, preferably a jet mill and a bead mill, more preferably a jet mill.

The jet mill includes a pulverizer in which a fluid such as compressed air and the like is discharged from a nozzle to form high speed turbulent airflow in a jet mill, and materials to be pulverized (hereinafter, referred to as "raw material" in some cases) are allowed to collide mutually in the high speed turbulent airflow to pulverize the raw material, a pulverizer in which a raw material is conveyed by high speed airflow to allow the raw material to collide against a collision body, thereby causing pulverization of the raw material, and the like (see, "Advanced pulverization technology and application (sentan funsai gijutsu to oyo)" edited by The Association of Powder Process Industry and Engineering, JAPAN, published by limited private company NGT, p. 162).

The jet mill includes "swirling airflow type" and "loop type" in which raw materials are allowed to mutually collide to pulverize in a pulverization zone formed of a plurality of pulverization nozzles disposed in circulating airflow, "fluidized bed type" in which raw materials are pulverized by mutual collision or friction in a fluidized bed type" (see, "Advanced pulverization technology and application (sentan funsai gijutsu to oyo)" edited by The Association of Powder Process Industry and Engineering, JAPAN, published by limited private company NGT, p. 162), "supersonic type" and the like, in addition to "collision type" in which raw materials are allowed to mutually collide or a raw material is allowed to collide against a collision body (target), thereby causing pulverization thereof as described above.

Commercial products of the jet mill include Cross Jet Mill (KURIMOTO, Ltd.), Jet-O-Mill, A-O Jet Mill, Sanitary AOM, Co-Jet, Single Track Jet Mill, Super STJ Mill (SEISHIN ENTERPRISE Co., Ltd.), Current Jet Mill (Nisshin Engineering Inc.), Ulmax (NISSO Engineering Co., Ltd.), Supersonic Jet Pulverizer type PJM, Supersonic Jet Pulverizer type CPY, Supersonic Jet Pulverizer type LJ-3, Supersonic Jet Pulverizer type I (Nippon Pneumatic Mfg. Co., Ltd.), Counter Jet Mill, Micro Jet type T, Spiral Jet Mill, Micron Jet MJQ (Hosokawa Micron Corporation), Fluidized Bed Jet Mill (Mitsui Mining Co., Ltd.), Nano Grinding Mill (TOKUJU Corporation), and the like (see, "Comminution, Classification and Surface Modification" edited by The Society of Powder Technology, JAPAN, published by limited private company NGT, p. 121).

In the present invention, "swirling airflow type" jet mills and "supersonic type" jet mills are preferably used, Supersonic Jet Pulverizer type PJM (Nippon Pneumatic Mfg. Co., Ltd.), A-O jet mill, Single Track Jet Mill (SEISHIN ENTERPRISE Co., Ltd.) and the like are more preferably used.

The parameters correlated with pulverization conditions of the jet mill include the compressed air feeding amount, the consumed air quantity, the raw material feeding amount, the treating amount, the raw material feeding rate, the pulverization pressure, the nozzle original pressure and the like.

Regarding the pulverization conditions in the present invention, the compressed air feeding amount is usually 0.12 to 41.4 $Nm^3$/min, the raw material feeding rate is usually 0.004 to 1200 kg/h, and the pulverization pressure is usually 0.1 to 1.6 MPa. The pulverization conditions in the present invention are selected according to the kind of the jet mill and the median diameter (50% D) of the resultant particles.

The material of the inner part of the jet mill includes alumina, ceramic, SUS, Teflon (registered trademark), urethane and the like.

A hammer mill is an apparatus in which a raw material is pulverized by impact and friction by rotating a cylinder having a lot of hammers mounted on the periphery thereof.

A bead mill is an apparatus in which a raw material is pulverized by filling beads (media) in a vessel and rotating the vessel. A dry bead mill is an apparatus in which a raw material is pulverized in a vapor phase or vacuum, and a wet bead mill is an apparatus in which a slurry prepared by mixing a raw material with liquid is added into a mill and stirred, thereby grinding and pulverizing the raw material. The diameter of the bead is 0.1 to 2 mm, and the material of the bead is glass, ceramic, metal and the like.

A turbo mill is an apparatus in which a raw material is pulverized by blades rotating at high speed and high speed swirling flow generating behind them.

By pulverizing particles of a compound represented by formula (I) (hereinafter, referred to as "compound (I)" in some cases) with a median diameter (50% D) of over 100 μm (hereinafter, referred to as "particle (I)" in some cases) by using a pulverizer in the presence of at least one member selected from the group consisting of silica, talc and clay (hereinafter, referred to as "inorganic particle" in some cases), adhesion of a raw material to the inner part of the pulverizer can be prevented and particles of uniform median diameter (50% D) are stably obtained. By preventing adhesion of a raw material, the raw material does not accumulate in the pulverizer, thus, it becomes unnecessary to take apart and wash the pulverizer, and the pulverizer can be operated continuously with ease.

Particles are arranged in ascending order from particles with smaller diameters, and the diameter of a particle at 50% on a volume basis is called "median diameter (50% D)". Particles are arranged in ascending order from particles with smaller diameters, and the diameter of a particle at 95% on a volume basis is called "95% particle diameter (95% D)".

The inorganic particle may be charged into a pulverizer before charging particles (I) into the pulverizer, or may be previously mixed with particles (I) before charging into the pulverizer. It is preferable that the inorganic particle is previously mixed with particles (I) before charging into the pulverizer.

Regarding the mixing ratio of particles (I) and the inorganic particle, the amount of the inorganic particle is preferably 0.01 to 19 parts by mass, more preferably 0.1 to 9 parts by mass, further preferably 0.4 to 4 parts by mass with respect to 1 part by mass of particles (I).

According to the process of the present invention, particles (I) can be pulverized by using a pulverizer in the presence of the inorganic particle to obtain a mixture of particles of a compound (I) with a median diameter (50% D) of 100 μm or less (hereinafter, referred to as "atomized particles (I)" in some cases) and at least one member selected from the group consisting of silica, talc and clay with a median diameter (50% D) of 100 μm or less (hereinafter, referred to as "atomized inorganic particle" in some cases).

Examples of silica include $SiO_2$ and $SiO_2 \cdot nH_2O$, $SiO_2 \cdot nH_2O$ is hydrous silicon dioxide having a CAS registry number of 7631-86-9.

Examples of silica include commercial products such as "AQ", "AQ-N", "ER", "ER-R", "NA" and "VN3" manufactured by Tosoh Silica Corporation, "Ultrasil (registered trademark) VN3", "Ultrasil (registered trademark) VN2", "Ultrasil (registered trademark) VN 2 GR", "Ultrasil (registered trademark) 360", "Ultrasil (registered trademark) 7000", "Ultrasil (registered trademark) 800" and "Ultrasil (registered trademark) AS7" manufactured by Degussa, "Zeosil (registered trademark) 115GR", "Zeosil (registered trademark) 1115 MP", "Zeosil (registered trademark) 1205 MP", "Zeosil (registered trademark) Z85MP", "Zeosil (registered trademark) 1165 MP", "Zeosil (registered trademark) 165GR", "Zeosil (registered trademark) 175GR" and "ZHRS (registered trademark) 1200 MP" manufactured by Rhodia, "Nipsil (registered trademark) AQ" manufactured by Nippon Silica K.K., and the like.

<Compound Represented by Formula (I) (Hereinafter, Referred to as "Compound (I)" in Some Cases)>

The alkyl group having 1 to 6 carbon atoms represented by $R^1$ and $R^2$ includes a methyl group, an ethyl group, a n-propyl group, an isopropyl group, a n-butyl group, an isobutyl group, a sec-butyl group, a tert-butyl group, a heptyl group and a hexyl group.

When $R^1$ and $R^2$ are linked to each other to form a ring together with the nitrogen atom to which they are bound, the polymethylene group formed by linking $R^1$ and $R^2$ to each other includes an ethylene group (dimethylene group), a trimethylene group, a tetramethylene group, a pentamethylene group, a hexamethylene group and the like. $R^1$ and $R^2$ are preferably a hydrogen atom.

$M^{n+}$ includes $H^+$, a lithium ion, a sodium ion, a potassium ion, a cesium ion, a magnesium ion, a calcium ion, a strontium ion, a barium ion, a manganese ion, an iron ion, a copper ion, a zinc ion and the like, preferably $H^+$ and alkali metal ions, more preferably $H^+$ and a sodium ion.

The compound (I) includes S-(aminoalkyl)thiosulfuric acids, S-(aminoalkyl)thiosulfates, S—(N,N-dialkylaminoalkyl)thiosulfuric acids, S—(N,N-dialkylaminoalkyl)thiosulfates, S—(N-monoalkylaminoalkyl)thiosulfuric acids, S—(N-monoalkylaminoalkyl)thiosulfates and the like, preferably S-(aminoalkyl)thiosulfuric acids and S-(aminoalkyl)thiosulfates.

The S-(aminoalkyl)thiosulfuric acids include S-(aminoethyl)thiosulfuric acid, S-(aminopropyl)thiosulfuric acid, S-(aminobutyl)thiosulfuric acid, S-(aminopentyl)thiosulfuric acid, S-(aminohexyl)thiosulfuric acid, S-(aminoheptyl)thiosulfuric acid, S-(aminooctyl)thiosulfuric acid, S-(aminononyl)thiosulfuric acid and the like.

The S-(aminoalkyl)thiosulfates include sodium S-(aminoethyl)thiosulfate, sodium S-(aminopropyl)thiosulfate, sodium S-(aminobutyl)thiosulfate, sodium S-(aminopentyl)thiosulfate, sodium S-(aminohexyl)thiosulfate, sodium S-(aminoheptyl)thiosulfate, sodium S-(aminooctyl)thiosulfate, sodium S-(aminononyl)thiosulfate and the like.

The S—(N,N-dialkylaminoalkyl)thiosulfuric acids include S—(N,N-dimethylaminoethyl)thiosulfuric acid, S—(N,N-dimethylaminopropyl)thiosulfuric acid, S—(N,N-dimethylaminobutyl)thiosulfuric acid, S—(N,N-dimethylaminopentyl)thiosulfuric acid, S—(N,N-dimethylaminohexyl)thiosulfuric acid, S—(N,N-dimethylaminoheptyl)thiosulfuric acid, S—(N,N-dimethylaminooctyl)thiosulfuric acid, S—(N,N-dimethylaminononyl)thiosulfuric acid and the like.

The S—(N,N-dialkylaminoalkyl)thiosulfates include sodium S—(N,N-dimethylaminoethyl)thiosulfate, sodium S—(N,N-dimethylaminopropyl)thiosulfate, sodium S—(N,N-dimethylaminobutyl)thiosulfate, sodium S—(N,N-dimethylaminopentyl)thiosulfate, sodium S—(N,N-dimethylaminohexyl)thiosulfate, sodium S—(N,N-dimethylaminoheptyl)thiosulfate, sodium S—(N,N-dimethylaminooctyl)thiosulfate, sodium S—(N,N-dimethylaminononyl)thiosulfate, and the like.

The S—(N-monoalkylaminoalkyl)thiosulfuric acids include S—(N-methylaminoethyl)thiosulfuric acid, S—(N-methylaminopropyl)thiosulfuric acid, S—(N-methylaminobutyl)thiosulfuric acid, S—(N-methylaminopentyl)thiosulfuric acid, S—(N-methylaminohexyl)thiosulfuric acid, S—(N-methylaminoheptyl)thiosulfuric acid, S—(N-methylaminooctyl)thiosulfuric acid, S—(N-methylaminononyl)thiosulfuric acid, and the like.

The S—(N-monoalkylaminoalkyl)thiosulfates include sodium S—(N-methylaminoethyl)thiosulfate, sodium S—(N-methylaminopropyl)thiosulfate, sodium S—(N-methylaminobutyl)thiosulfate, sodium S—(N-methylaminopentyl)thiosulfate, sodium S—(N-methylaminohexyl)thiosulfate, sodium S—(N-methylaminoheptyl)thiosulfate, sodium S—(N-methylaminooctyl)thiosulfate, sodium S—(N-methylaminononyl)thiosulfate, and the like.

The compound (I) can be obtained, for example, by reacting a compound represented by formula (II) and a hydrogen halide to obtain a hydrohalide of the compound represented by formula (III), and reacting the resultant hydrohalide of the compound represented by formula (III) and a metal salt of thiosulfuric acid.

(II)

(in formula (II), $R^3$ represents a hydroxyl group or an alkoxy group having 1 to 8 carbon atoms.

$R^1$, $R^2$ and m represent the same meaning as described above.)

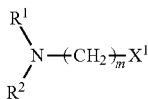

$$\begin{array}{c} R^1 \\ \diagdown \\ N-\!\!\!+\!\!CH_2\!\!\!+\!\!\!\!_m X^1 \\ \diagup \\ R^2 \end{array} \quad (III)$$

(in formula (III), $X^1$ represents a halogen atom.

$R^1$, $R^2$ and m represent the same meaning as described above.)<

<Compound Represented by Formula (II) (Hereinafter, Referred to as "Compound (II)" in Some Cases)>

$R^3$ includes a hydroxyl group.

The alkoxy group having 1 to 8 carbon atoms represented by $R^3$ includes a methoxy group, an ethoxy group, a n-propyloxy group, an isopropyloxy group, a n-butyloxy group, an isobutyloxy group, a sec-butyloxy group, a tert-butyloxy group, a n-pentyloxy group, a n-hexyloxy group, a cyclohexyloxy group, a n-heptyloxy group, a n-octyloxy group, a 2-ethylhexyloxy group and the like. $R^3$ is preferably a methoxy group.

The compound (II) includes, for example, 2-hydroxyethylamine, 3-hydroxypropylamine, 4-hydroxybutylamine, 5-hydroxypentylamine, 6-hydroxyhexylamine, 7-hydroxyheptylamine, 8-hydroxyoctylamine, 9-hydroxynonylamine, N-methyl-3-hydroxypropylamine, N-ethyl-3-hydroxypropylamine, N-n-propyl-3-hydroxypropylamine, N-isopropyl-3-hydroxypropylamine, N,N-dimethyl-3-hydroxypropylamine, N-ethyl-N-methyl-3-hydroxypropylamine, (3-hydroxypropyl)piperidine, 2-methoxyethylamine, 3-methoxypropylamine, 4-methoxybutylamine, 5-methoxypentylamine, 6-methoxyhexylamine, 7-methoxyheptylamine, 8-methoxyoctylamine, 9-methoxynonylamine, N-methyl-3-methoxypropylamine, N-ethyl-3-methoxypropylamine, N-n-propyl-3-methoxypropylamine, N-isopropyl-3-methoxypropylamine, N,N-dimethyl-3-methoxypropylamine, N-ethyl-N-methyl-3-methoxypropylamine, (3-methoxypropyl)piperidine, 2-ethoxyethylamine, 3-ethoxypropylamine, 4-ethoxybutylamine, 5-ethoxypentylamine, 6-ethoxyhexylamine, 7-ethoxyheptylamine, 8-ethoxyoctylamine, 9-ethoxynonylamine, N-methyl-3-ethoxypropylamine, N-ethyl-3-ethoxypropylamine, N-n-propyl-3-ethoxypropylamine, N-isopropyl-3-ethoxypropylamine, N,N-dimethyl-3-ethoxypropylamine, N-ethyl-N-methyl-3-ethoxypropylamine, (3-ethoxypropyl)piperidine, 2-n-propyloxyethylamine, 3-n-propyloxypropylamine, 4-n-propyloxybutylamine, 5-n-propyloxypentylamine, 6-propyloxyhexylamine, 7-propyloxyheptylamine, 8-propyloxyoctylamine, 9-propyloxynonylamine, N-methyl-3-n-propyloxypropylamine, N-ethyl-3-n-propyloxypropylamine, N-n-propyl-3-n-propyloxypropylamine, N-isopropyl-3-n-propyloxypropylamine, N,N-dimethyl-3-n-propyloxypropylamine, N-ethyl-N-methyl-3-n-propyloxypropylamine, (3-n-propyloxypropyl)piperidine, 2-isopropyloxyethylamine, 3-isopropyloxypropylamine, 4-isopropyloxybutylamine, 5-isopropyloxypentylamine, 6-isopropyloxyhexylamine, 7-isopropyloxyheptylamine, 8-isopropyloxyoctylamine, 9-isopropyloxynonylamine, N-methyl-3-isopropyloxypropylamine, N-ethyl-3-isopropyloxypropylamine, N-n-propyl-3-isopropyloxypropylamine, N-isopropyl-3-isopropyloxypropylamine, N,N-dimethyl-3-isopropyloxypropylamine, N-ethyl-N-methyl-3-isopropyloxypropylamine, (3-isopropyloxypropyl)piperidine, 3-n-butyloxypropylamine, N-methyl-3-n-butyloxypropylamine, N-ethyl-3-n-butyloxypropylamine, N-n-propyl-3-n-butyloxypropylamine, N-isopropyl-3-n-butyloxypropylamine, N,N-dimethyl-3-n-butyloxypropylamine, N-ethyl-N-methyl-3-n-butyloxypropylamine, (3-n-butyloxypropyl)piperidine, 3-isobutyloxypropylamine, N-methyl-3-isobutyloxypropylamine, N-ethyl-3-isobutyloxypropylamine, N-n-propyl-3-isobutyloxypropylamine, N-isopropyl-3-isobutyloxypropylamine, N,N-dimethyl-3-isobutyloxypropylamine, N-ethyl-N-methyl-3-isobutyloxypropylamine, (3-isobutyloxypropyl)piperidine, 3-sec-butyloxypropylamine, N-methyl-3-sec-butyloxypropylamine, N-ethyl-3-sec-butyloxypropylamine, N-n-propyl-3-sec-butyloxypropylamine, N-isopropyl-3-sec-butyloxypropylamine, N,N-dimethyl-3-sec-butyloxypropylamine, N-ethyl-N-methyl-3-sec-butyloxypropylamine, (3-sec-butyloxypropyl)piperidine, 3-tert-butyloxypropylamine, N-methyl-3-tert-butyloxypropylamine, N-ethyl-3-tert-butyloxypropylamine, N-n-propyl-3-tert-butyloxypropylamine, N-isopropyl-3-tert-butyloxypropylamine, N,N-dimethyl-3-tert-butyloxypropylamine, N-ethyl-N-methyl-3-tert-butyloxypropylamine, (3-tert-butyloxypropyl)piperidine, 3-n-pentyloxypropylamine, N-methyl-3-n-pentyloxypropylamine, N-ethyl-3-n-pentyloxypropylamine, N-n-propyl-3-n-pentyloxypropylamine, N-isopropyl-3-n-pentyloxypropylamine, N,N-dimethyl-3-n-pentyloxypropylamine, N-ethyl-N-methyl-3-n-pentyloxypropylamine, (3-n-pentyloxypropyl)piperidine, 3-n-hexyloxypropylamine, N-methyl-3-n-hexyloxypropylamine, N-ethyl-3-n-hexyloxypropylamine, N-n-propyl-3-n-hexyloxypropylamine, N-isopropyl-3-n-hexyloxypropylamine, N,N-dimethyl-3-n-hexyloxypropylamine, N-ethyl-N-methyl-3-n-hexyloxypropylamine, (3-n-hexyloxypropyl)piperidine, 3-n-heptyloxypropylamine, N-methyl-3-n-heptyloxypropylamine, N-ethyl-3-n-heptyloxypropylamine, N-n-propyl-3-n-heptyloxypropylamine, N-isopropyl-3-n-heptyloxypropylamine, N,N-dimethyl-3-n-heptyloxypropylamine, N-ethyl-N-methyl-3-n-heptyloxypropylamine, (3-n-heptyloxypropyl)piperidine, 3-n-octyloxypropylamine, N-methyl-3-n-octyloxypropylamine, N-ethyl-3-n-octyloxypropylamine, N-n-propyl-3-n-octyloxypropylamine, N-isopropyl-3-n-octyloxypropylamine, N,N-dimethyl-3-n-octyloxypropylamine, N-ethyl-N-methyl-3-n-octyloxypropylamine, (3-n-octyloxypropyl)piperidine, 2-(2-ethylhexyloxy)ethylamine, 3-(2-ethylhexyloxy)propylamine, 4-(2-ethylhexyloxy)butylamine, 5-(2-ethylhexyloxy)pentylamine, N-methyl-3-(2-ethylhexyloxy)propylamine, N-ethyl-3-(2-ethylhexyloxy)propylamine, N-n-propyl-3-(2-ethylhexyloxy)propylamine, N-isopropyl-3-(2-ethylhexyloxy)propylamine, N,N-dimethyl-3-(2-ethylhexyloxy)propylamine, N-ethyl-N-methyl-3-(2-ethylhexyloxy)propylamine, [3-(2-ethylhexyloxy)propyl]piperidine and the like, preferably compounds in which m=3 and $R^1$ and $R^2$ represent a hydrogen atom such as 3-methoxypropylamine, 3-ethoxypropylamine, 3-n-propyloxypropylamine, 3-isopropyloxypropylamine, 3-n-butyloxypropylamine, 3-isobutyloxypropylamine, 3-sec-butyloxypropylamine, 3-tert-butyloxypropylamine, 3-n-pentyloxypropylamine, 3-n-hexyloxypropylamine, 3-n-heptyloxypropylamine, 3-n-octyloxypropylamine and 3-(2-ethylhexyloxy)propylamine, and especially, 3-methoxypropylamine is more preferable.

Commercial products of the compound (II) include 3-hydroxypropylamine (Tokyo Chemical Industry Co., Ltd.), 3-methoxypropylamine (Tokyo Chemical Industry Co., Ltd.), 3-ethoxypropylamine (Tokyo Chemical Industry Co., Ltd.), 3-n-propyloxypropylamine (Tokyo Chemical Industry Co., Ltd.), 3-isopropyloxypropylamine (Tokyo Chemical Industry Co., Ltd.), 3-n-butyloxypropylamine (Tokyo Chemical Industry Co., Ltd.), 3-(2-ethylhexyloxy)propylamine (Tokyo Chemical Industry Co., Ltd.) and the like.

The process for producing the compound (II) includes, for example, a process represented by the following formula. The compound (II) can be produced by catalytically reducing acrylonitrile in an alcohol under a hydrogen atmosphere using Raney nickel, then, if necessary, performing N-alkylation.

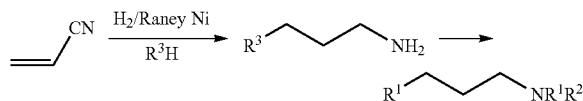

($R^1$, $R^2$ and $R^3$ represent the same meaning as described above.).

<Hydrogen Halide>

The hydrogen halide includes hydrogen fluoride, hydrogen chloride, hydrogen bromide and hydrogen iodide, preferably hydrogen chloride and hydrogen bromide, more preferably hydrogen chloride.

<Hydrohalide of Compound Represented by Formula (III) (Hereinafter, Referred to as "Compound (III)" in Some Cases) (Hereinafter, Referred to as "Salt (III)" in Some Cases)>

The halogen atom represented by $X^1$ includes a fluorine atom, a chlorine atom, a bromine atom and an iodine atom, preferably a chlorine atom.

The compound (III) includes 2-fluoroethylamine, 2-chloroethylamine, 2-bromoethylamine, 2-iodoethylamine, 3-fluoropropylamine, 3-chloropropylamine, 3-bromopropylamine, 3-iodopropylamine, 4-fluorobutylamine, 4-chlorobutylamine, 4-n-bromobutylamine, 4-iodobutylamine, 5-fluoropentylamine, 5-chloropentylamine, 5-bromopentylamine, 5-iodopentylamine, 6-chlorohexylamine, 7-chloroheptylamine, 8-chlorooctylamine, 9-chlorononylamine and the like.

The acid which forms a salt with a compound (III) includes, for example, hydrochloric acid, hydrobromic acid and the like. The acid is preferably hydrochloric acid.

<Step of Reacting Compound (II) and Hydrogen Halide>

By reacting a compound (II) and a hydrogen halide, a hydrohalide of a compound (III) (hereinafter, referred to as "salt (III)" in some cases) is obtained.

The use amount of a hydrogen halide is 200 to 1500 mol, preferably 300 to 1000 mol, more preferably 300 to 900 mol with respect to 100 mol of the compound (II).

The reaction of a compound (II) and a hydrogen halide is carried out in the absence of an organic solvent, or in the presence of a solvent which is inactive for the compound (II) and the hydrogen halide, and preferably carried out in the absence of an organic solvent.

<Post Treatment Step>

After completion of the reaction of a compound (II) and a hydrogen halide, the resultant mixture is subjected to a cooling treatment under normal pressure to cause deposition of a salt (III), and if necessary, a liquid phase and a solid phase are separated by performing a treatment such as filtration and the like, thus a salt (III) can be isolated.

The resultant salt (III) can be used in the subsequent reaction by dissolving in a solvent. The solvent for dissolution includes, for example, water or organic solvents. By adding an inorganic acid such as sodium hydroxide, hydrofluoric acid, hydrobromic acid, hydrochloric acid, sulfuric acid, phosphoric acid, boric acid and the like or an organic acid such as acetic acid, p-toluenesulfonic acid and the like to a solution containing the salt (III) to control pH thereof, the solution containing the salt (III) can be used as it is in the subsequent step ("step of reacting salt (III) and metal salt of thiosulfuric acid" described later). pH of the solution containing the salt (III) is usually 1 to 7, preferably 2 to 5, more preferably 2 to 3.5.

<Step of Reacting Salt (III) and Metal Salt of Thiosulfuric Acid>

By reacting a salt (III) and a metal salt of thiosulfuric acid, a compound (I) is obtained.

The metal salt of thiosulfuric acid includes sodium thiosulfate, potassium thiosulfate, calcium thiosulfate and the like, preferably sodium thiosulfate. The metal salt of thiosulfuric acid may be a hydrate.

The use amount of the metal salt of thiosulfuric acid is preferably 80 to 500 mol, more preferably 90 to 200 mol, further preferably 100 to 110 mol with respect to 100 mol of a salt (III).

The reaction of a salt (III) and a metal salt of thiosulfuric acid is carried out in the absence of an organic solvent, or in the presence of a solvent which is inactive for the salt (III) and the metal salt of thiosulfuric acid, and preferably carried out in the presence of the solvent. The solvent is preferably a solvent capable of dissolving the metal salt of thiosulfuric acid, and includes alcohols having 1 to 4 carbon atoms, water, a mixed solvent composed of an alcohol having 1 to 4 carbon atoms and water, and the like. Water, and a mixed solvent composed of an alcohol having 1 to 4 carbon atoms and water are preferable, and water is more preferable.

The use amount of a solvent is 0.5 parts to 40 parts, preferably 1 part to 20 parts, more preferably 1.5 parts to 10 parts with respect to 1 part of a salt (III).

<Step of Taking Out Compound (I)>

After completion of the reaction of a salt (III) and a metal salt of thiosulfuric acid, condensation, purification or the like is preferably carried out to allow a compound (I) to deposit in the resultant mixture and to take out the compound (I) from the mixture.

The compound (I) obtained as described above can be isolated as a solid, for example, by an operation of condensation, crystallization and the like.

The median diameter (50% D) of atomized particles (I) is usually 100 µm or less, preferably 70 µm or less, more preferably 40 µm or less, further preferably less than 10 µm. The lower limit thereof is preferably 1 µm or more. The median diameter (50% D) can be measured by a laser diffraction method. When the median diameter is in the above-described range, the dispersibility of atomized particles (I) in vulcanized rubber is good, and the viscoelastic property of vulcanized rubber containing atomized particles (I) tends to be improved. The median diameter (50% D) of a mixture of atomized particles (I) and atomized inorganic particles is used as the median diameter (50% D) of atomized particles (I).

The 95% particle diameter (95% D) of atomized particles (I) is usually 150 µm or less, preferably 100 µm or less, more preferably 50 µm or less, further preferably 40 µm or less. The lower limit thereof is preferably 1 µm or more. The 95% particle diameter (95% D) can be measured by a laser diffraction method. When the 95% particle diameter is in the above-described range, the dispersibility of atomized particles (I) in vulcanized rubber is good, and the viscoelastic property of vulcanized rubber containing atomized particles (I) tends to be improved. The 95% particle diameter (95% D) of a mixture of atomized particles (I) and atomized inorganic particles is used as the 95% particle diameter (95% D) of atomized particles (I).

A mixture of atomized particles (I) and atomized inorganic particles is compression-molded by a roll press machine and the like, to obtain lowered static bulk density and attain easy handling.

Next, a step (A) of kneading atomized particles (I), a rubber component and a filler will be explained.

The use amount of atomized particles (I) is preferably in the range of 0.1 to 10 parts by mass with respect to 100 parts by mass of a rubber component described later. More preferably, the use amount is in the range of 0.4 to 3 parts by mass.

In the step (A), atomized particles (I) may be subjected to kneading, or a mixture of atomized particles (I) and atomized inorganic particles may be subjected to kneading.

The rubber component includes natural rubber, epoxidated natural rubber, deproteinized natural rubber and other modified natural rubbers, and additionally exemplified are various synthetic rubbers such as polyisoprene rubber (IR), styrene•butadiene copolymerized rubber (SBR), polybutadiene rubber (BR), acrylonitrile•butadiene copolymerized rubber (NBR), isoprene•isobutylene copolymerized rubber (IIR), ethylene•propylene•diene copolymerized rubber (EPDM), halogenated butyl rubber (HR) and the like, and highly unsaturated rubbers such as natural rubber, styrene•butadiene copolymerized rubber, polybutadiene rubber and the like are preferably used. Natural rubber is particularly preferable. Further, it is effective to combine several types of rubber components, such as a combination of natural rubber and styrene•butadiene copolymerized rubber, a combination of natural rubber and polybutadiene rubber, and the like.

Examples of the natural rubber include natural rubbers of grades such as RSS#1, RSS#3, TSR20, SIR20 and the like. As the epoxidated natural rubber, those having a degree of epoxidation of 10 to 60% by mol are preferable, and for example, ENR25 and ENR50 manufactured by kun Poulenc Guthrie Inc. are exemplified. As the deproteinized natural rubber, deproteinized natural rubbers having a total nitrogen content of 0.3% by mass or less are preferable. As the modified natural rubber, modified natural rubbers containing a polar group obtained by previously reacting 4-vinylpyridine, N,N,-dialkylaminoethyl acrylate (for example, N,N,-diethylaminoethyl acrylate), 2-hydroxy acrylate and the like with natural rubber are preferably used.

Examples of SBR include emulsion polymerized SBRs and solution polymerized SBRs described in "Rubber Industry Handbook <fourth edition>", pp. 210 to 211, edited by The Society of Rubber Science and Technology, Japan. Especially, solution polymerized SBRs are preferably used as the rubber composition for tread, and further, particularly preferably used are commercially marketed products of solution polymerized SBRs having a molecular end modified using 4,4'-bis(dialkylamino)benzophenone such as "Nipol (registered trademark) NS116" manufactured by ZEON Corporation and the like, solution polymerized SBRs having a molecular end modified using a halogenated tin compound such as "SL574" manufactured by JSR Corporation, and the like and silane-modified solution polymerized SBRs such as "E10" and "E15" manufactured by Asahi Kasei Corporation and the like, and solution polymerized SBRs having any of nitrogen, tin and silicon or a combination thereof at the molecular end obtained by using singly any of a lactam compound, an amide compound, a urea-based compound, an N,N-dialkylacrylamide compound, an isocyanate compound, an imide compound, a silane compound having an alkoxy group (trialkoxysilane compound and the like) and an aminosilane compound or by using two or more of the above-described several different compounds such as a tin compound and a silane compound having an alkoxy group, an alkylacrylamide compound and a silane compound having an alkoxy group, and the like and modifying the end thereof. Further, oil-extended SBRs obtained by adding an oil such as a process oil, an aroma oil and the like to emulsion polymerized SBR and solution polymerized SBR after polymerization can be preferably used as the rubber composition for tread, and the like.

As examples of BR, solution polymerized BRs such as high cis BRs having a cis 1,4 linkage content of 90% or more and low cis BRs having a cis linkage content of around 35%, and the like are exemplified, and low cis BRs having a high vinyl content are preferably used. Further, particularly preferably used are tin-modified BRs such as "Nipol (registered trademark) BR 1250H" manufactured by ZEON Corporation and the like, and solution polymerized BRs having any of nitrogen, tin and silicon or a combination thereof at the molecular end obtained by using singly any of 4,4'-bis(dialkylamino)benzophenone, a halogenated tin compound, a lactam compound, an amide compound, a urea-based compound, an N,N-dialkylacrylamide compound, an isocyanate compound, an imide compound, a silane compound having an alkoxy group (trialkoxysilane compound and the like) and an aminosilane compound or by using two or more of the above-described several different compounds such as a tin compound and a silane compound having an alkoxy group, an alkylacrylamide compound and a silane compound having an alkoxy group, and the like and modifying the end thereof. These BRs can be preferably used as the rubber composition for tread and the rubber composition for side wall, and usually used in a blend with SBR and/or natural rubber. Regarding the blending ratio, it is preferable for the rubber composition for tread that the content of SBR and/or natural rubber is 60 to 100% by mass and the content of BR is 40 to 0% by mass with respect to the total rubber weight, it is preferable for the rubber composition for side wall that the content of SBR and/or natural rubber is 10 to 70% by mass and the content of BR is 90 to 30% by mass with respect to the total rubber weight, and further, a blend having a content of natural rubber of 40 to 60% by mass and a content of BR of 60 to 40% by mass with respect to the total rubber weight is particularly preferable. In this case, a blend of modified SBR and non-modified SBR, and a blend of modified BR and non-modified BR are also preferable.

A filler is usually contained in vulcanized rubber constituting a tire. As the filler, exemplified are carbon black, silica, talc, clay, aluminum hydroxide, titanium oxide and the like usually used in the field of rubber, and carbon black and silica are preferably used, and further, carbon black is particularly preferably used. The carbon black includes, for example, those described in "Rubber Industry Handbook <Fourth edition>" p. 494, edited by The Society of Rubber Science and Technology, Japan, and preferable are carbon blacks such as HAF (High Abrasion Furnace), SAF (Super Abrasion Furnace), ISAF (Intermediate SAF), FEF (Fast Extrusion Furnace), MAF, GPF (General Purpose Furnace), SRF (Semi-Reinforcing Furnace) and the like. For the rubber composition for tire tread, carbon blacks having a CTAB (Cetyl Tri-methyl Ammonium Bromide) surface area of 40 to 250 m$^2$/g, a nitrogen adsorption specific surface area of 20 to 200 m$^2$/g and a particle size of 10 to 50 nm are preferably used, carbon blacks having a CTAB surface area of 70 to 180 m$^2$/g are further preferable, and examples thereof include N110, N220, N234, N299, N326, N330, N330T, N339, N343, N351 and the like according to the standard of ASTM. Also preferable are surface-treated carbon blacks prepared by adsorbing silica to the surface of carbon black in an amount of 0.1 to 50% by mass. Further, it is effective to combine several kinds of fillers such as a combination of carbon black and silica, and the like, and it is preferable for the rubber composition for tire tread that carbon black is used singly or both carbon black and silica are used. For the rubber composition for carcass or side wall, carbon blacks having a CTAB surface area of 20 to 60 m$^2$/g and a particle size of 40 to 100 nm are preferably used, and examples thereof include N330, N339, N343, N351, N550, N568, N582, N630, N642, N660, N662, N754, N762 and the like according to the standard of ASTM. Though the use amount of such a filler is not particularly restricted, the use amount is preferably in the range of 5 to 100 parts by mass with respect to 100 parts by mass of a rubber component. When only carbon black is used as the filler, it is particularly preferably 30 to 80 parts by mass with respect to 100 parts by mass of a rubber component, and when carbon black is used together with silica in a tread member application, the amount of carbon black is particularly preferably 5 to 60 parts by mass with respect to 100 parts by mass of a rubber component.

As the silica used as the filler, silicas having a CTAB specific surface area of 50 to 180 m$^2$/g and silicas having a nitrogen adsorption specific surface area of 50 to 300 m$^2$/g are exemplified, and preferably used are commercially available products such as "AQ" and "AQ-N" manufactured by Tosoh Silica Corporation, "Ultrasil (registered trademark) VN3", "Ultrasil (registered trademark) VN3-G", "Ultrasil (registered trademark) 360" and "Ultrasil (registered trademark) 7000" manufactured by Degussa, "Zeosil (registered trademark) 115GR", "Zeosil (registered trademark) 1115 MP", "Zeosil (registered trademark) 1205 MP" and "Zeosil (registered trademark) Z85MP" manufactured by Rhodia, "Nipsil (registered trademark) AQ" manufactured by Nippon Silica Industrial Co., Ltd., and the like. It is also preferable to blend silicas having a pH of 6 to 8, silicas containing sodium in an amount of 0.2 to 1.5% by mass, spherical silicas having a roundness of 1 to 1.3, silicas surface-treated with a silicone oil such as dimethylsilicone oil and the like, an organosilicon compound containing an ethoxysilyl group or an alcohol such as ethanol, polyethylene glycol and the like, or silicas having two or more different nitrogen adsorption specific surface areas.

Though the use amount of such a filler is not particularly restricted, silica is preferably used in the rubber composition for tread for automobile, and the use amount the filler is preferably in the range of 10 to 120 parts by mass with respect to 100 parts by mass of a rubber component. When silica is blended, it is preferable to blend carbon black in an amount of 5 to 50 parts by mass with respect to 100 parts by mass of a rubber component, and the blending ratio of silica/carbon black is particularly preferably 0.7/1 to 1/0.1. When silica is usually used as the filler, it is preferable to add a compound having an element such as silicon and the like or a functional group such as alkoxysilane and the like capable of bonding to silica, such as one or more silane coupling agents selected from the group consisting of bis (3-triethoxysilylpropyl)tetrasulfide (manufactured by Degussa, "Si-69"), bis(3-triethoxysilylpropyl)disulfide (manufactured by Degussa, "Si-75"), bis(3-diethoxymethylsilylpropyl)tetrasulfide, bis(3-diethoxymethylsilylpropyl) disulfide, octanethioic acid S—[3-(triethoxysilyl)propyl]ester (manufactured by General Electronic Silicones, "NXT silane"), octanethioic acid S—[3-{(2-methyl-1,3-propanedialkoxy)ethoxysilyl}propyl]ester and octanethioic acid S—[3-{(2-methyl-1,3-propanedialkoxy) methylsilyl}propyl]ester phenyltriethoxysilane, methyltrimethoxysilane, methyltriethoxysilane, methyltriacetoxysilane, methyltributoxysilane, ethyltrimethoxysilane, ethyltriethoxysilane, isobutyltrimethoxysilane, isobutyltriethoxysilane, n-octyltrimethoxysilane, n-octyltriethoxysilane, vinyltrimethoxysilane, vinyltriethoxysilane, vinyltri (methoxyethoxy)silane, phenyltrimethoxysilane, phenyltriethoxysilane, phenyltriacetoxysilane, 3-methacryloxypropyltrimethoxysilane, 3-methacryloxypropyltriethoxysilane, 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, (3-glycidoxypropyl)trimethoxysilane, (3-glycidoxypropyl)triethoxysilane, 2-(3, 4-epoxycyclohexyl)ethyltrimethoxysilane, 2-(3,4-epoxycyclohexyl)ethyltriethoxysilane, 3-isocyanate propyltrimethoxysilane and 3-isocyanate propyltriethoxysilane, and particularly preferable are bis(3-triethoxysilylpropyl)tetrasulfide (manufactured by Degussa, "Si-69"), bis(3-triethoxysilylpropyl)disulfide (manufactured by Degussa, "Si-75") and 3-octanoylthiopropyltriethoxysilane (manufactured by General Electronic Silicones, "NXT silane"). Though the addition period of these compounds is not particularly restricted, it is preferable to blend these compounds into rubber simultaneously with silica, and the blending amount is preferably 2 to 10% by mass, further preferably 7 to 9% by mass with respect to silica. The blending temperature in blending is preferably in the range of 80 to 200° C., further preferably 110 to 180° C. Further, when silica is used as the filler, it is also preferable to blend a mono-hydric alcohol such as ethanol, butanol, octanol and the like, a di- or more-hydric alcohol such as ethylene glycol, diethylene glycol, triethylene glycol, polyethylene glycol, polypropylene glycol, pentaerythritol, polyether polyol and the like, an N-alkylamine, an amino acid, or a liquid polybutadiene having a carboxyl-modified or amine-modified molecular end, and the like, in addition to silica and a compound having an element such as silicon and the like or a functional group such as alkoxysilane and the like capable of bonding to silica.

As the aluminum hydroxide, exemplified are aluminum hydroxides having a nitrogen adsorption specific surface area of 5 to 250 m$^2$/g and aluminum hydroxides having a DOP oiling quantity of 50 to 100 ml/100 g.

It is preferable to blend zinc oxide and stearic acid, in addition to the atomized particles (I), the rubber component and the filler, and to knead them. The use amount of zinc oxide is preferably in the range of 1 to 15 parts by mass, more preferably in the range of 3 to 8 parts by mass with respect to 100 parts by mass of the rubber component. The use amount of stearic acid is preferably in the range of 0.5 to 10 parts by mass, more preferably in the range of 1 to 5 parts by mass with respect to 100 parts by mass of the rubber component.

Next, a step (B) of kneading the kneaded mixture obtained in the step (A), a sulfur component and a vulcanization accelerator will be explained. In the present specification, "unvulcanized rubber composition" denotes a rubber composition obtained in this step.

The sulfur component includes powdered sulfur, precipitated sulfur, colloidal sulfur, insoluble sulfur, highly-dispersible sulfur and the like. Usually, powdered sulfur is preferable, and in the case of use in a tire member having high sulfur content such as a member for belt and the like, insoluble sulfur is preferable. The above-described sulfur component does not include a compound (I) and metal salts thereof and a vulcanization accelerator. The use amount of the sulfur component is preferably in the range of 0.3 to 5 parts by mass, more preferably in the range of 0.5 to 3 parts by mass with respect to 100 parts by mass of the rubber component.

Examples of the vulcanization accelerator includes thiazole vulcanization accelerators, sulfenamide vulcanization accelerators and guanidine vulcanization accelerators described in Rubber Industry Handbook <Fourth edition> pp. 412 to 413 (published by The Society of Rubber Science and Technology, Japan on Jan. 20, 1994).

Specific examples thereof include N-cyclohexyl-2-benzothiazolyl sulfenamide (CBS), N-tert-butyl-2-benzothiazolyl sulfenamide (BBS), N,N-dicyclohexyl-2-benzothiazolyl sulfenamide (DCBS), 2-mercaptobenzothiazole (MBT), dibenzothiazyl disulfide (MBTS) and diphenylguanidine (DPG). Morpholine disulfide which is a known vulcanizing agent can also be used. In the case of use of carbon black as the filler, it is preferable to use N-cyclohexyl-2-benzothiazolyl sulfenamide (CBS), N-tert-butyl-2-benzothiazolyl sulfenamide (BBS), N,N-dicyclohexyl-2-benzothiazolyl sulfenamide (DCBS), dibenzothiazyl disulfide (MBTS) and diphenylguanidine (DPG) together, and when silica and carbon black are used together as the filler, it is preferable to use any of N-cyclohexyl-2-benzothiazolyl sulfenamide (CBS), N-tert-butyl-2-benzothiazolyl sulfenamide (BBS), N,N-dicyclohexyl-2-benzothiazolyl sulfenamide (DCBS) and dibenzothiazyl disulfide (MBTS), and diphenylguanidine (DPG) together. The vulcanization accelerator does not include a compound (I).

Though the ratio of sulfur to a vulcanization accelerator is not particularly restricted, the sulfur/vulcanization accelerator ratio is preferably in the range of 2/1 to 1/2 by weight. EV vulcanization in which the sulfur/vulcanization accelerator ratio is controlled to 1 or less as a method of improving the heat resistance of a rubber member composed mainly of natural rubber is preferably used in applications particularly needing an improvement in heat resistance.

Atomized particles (I) may be blended and kneaded in the step (B), however, it is preferable that atomized particles (I) are blended and kneaded in the step (A). The use amount of atomized particles (I) is preferably in the range of 0.1 to 10 parts by mass with respect to 100 parts by mass of the rubber component. More preferably, it is in the range of 0.4 to 3 parts by mass. When kneading in the step (A), kneading is accompanied by heat generation, and the temperature of a kneaded mixture in completion of kneading is preferably in the range of 140° C. to 180° C., more preferably in the range of 150° C. to 170° C. When the temperature of a kneaded mixture in completion of kneading is 140° C. or higher, the reaction of atomized particles (I) and a filler tends to progress efficiently, and when 180° C. or lower, there is a tendency that degradation and gelling of the rubber component are suppressed, and the viscoelastic property of the finally obtainable vulcanized rubber tends to be improved.

The kneading time is preferably 1 minute to 10 minutes, more preferably 2 minutes to 7 minutes. When the kneading time is 1 minute or more, dispersion of a filler in the rubber component tends to be better, and when the kneading time is 10 minutes or less, there is a tendency that degradation and gelling of the rubber component are suppressed, and the viscoelastic property of the finally obtainable vulcanized rubber tends to be improved.

It is also possible to blend and knead agents improving the viscoelastic property conventionally used in the field of rubber. Such agents include, for example, N,N'-bis(2-methyl-2-nitropropyl)-1,6-hexanediamine (manufactured by Sumitomo Chemical Co., Ltd., "Sumifine (registered trademark) 1162"), dithiouracil compounds described in JP-A No. 63-23942, nitrosoquinoline compounds such as 5-nitroso-8-hydroxyquinoline (NQ-58) and the like described in JP-A No. 60-82406, alkylphenol•sulfur chloride condensates described in JP-A No. 2009-138148 such as "Tackirol (registered trademark) AP, V-200" manufactured by Taoka Chemical Co., Ltd., "Vultac 2, 3, 4, 5, 7, 710" manufactured by Pennwalt Corp., and the like, bis(3-triethoxysilylpropyl) tetrasulfide (manufactured by Degussa, "Si-69"), bis(3-triethoxysilylpropyl)disulfide (manufactured by Degussa, "Si-75"), bis(3-diethoxymethylsilylpropyl)tetrasulfide, bis(3-diethoxymethylsilylpropyl)disulfide, octanethioic acid S—[3-(triethoxysilyl)propyl]ester, octanethioic acid S—[3-{(2-methyl-1,3-propanedialkoxy)ethoxysilyl}propyl]ester, and silane coupling agents such as octanethioic acid S—[3-{(2-methyl-1,3-propanedialkoxy)methylsilyl}propyl]ester phenyltriethoxysilane, methyltrimethoxysilane, methyltriethoxysilane, methyltriacetoxysilane, methyltributoxysilane, ethyltrimethoxysilane, ethyltriethoxysilane, isobutyltrimethoxysilane, isobutyltriethoxysilane, n-octyltrimethoxysilane, n-octyltriethoxysilane, vinyltrimethoxysilane, vinyltriethoxysilane, vinyltri(methoxyethoxy)silane, phenyltrimethoxysilane, phenyltriethoxysilane, phenyltriacetoxysilane, 3-methacryloxypropyltrimethoxysilane, 3-methacryloxypropyltriethoxysilane, 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, (3-glycidoxypropyl)trimethoxysilane, (3-glycidoxypropyl)triethoxysilane, 2-(3,4-epoxycyclohexyl)ethyltrimethoxysilane, 2-(3,4-epoxycyclohexyl)ethyltriethoxysilane, 3-isocyanate propyltrimethoxysilane, 3-isocyanate propyltriethoxysilane and the like, 1,6-bis(N,N'-dibenzylthiocarbamoyldithio)hexane (manufactured by Bayer, "KA9188"), 1,6-hexamethylene dithiosulfate disodium salt dihydrate, 1,3-biscitraconimidemethylbenzene (manufactured by Flexsys, "Perkalink 900"), 1-benzoyl-2-phenylhydrazide, carboxylic acid hydrazide derivatives such as 1- or 3-hydroxy-N'-(1-methylethylidene)-2-naphthoic acid hydrazide, and 1- or 3-hydroxy-N'-(1-methylpropylidene)-2-naphthoic acid hydrazide, 1- or 3-hydroxy-N'-(1,3-dimethylbutylidene)-2-naphthoic acid hydrazide and 1- or 3-hydroxy-N'-(2-furylmethylene)-2-naphthoic acid hydrazide and the like described in JP-A No. 2004-91505, 3-hydroxy-N'-(1,3-dimethylbutylidene)-2-naphthoic acid hydrazide, 3-hydroxy-N'-(1,3-diphenylethylidene)-2-naphthoic acid hydrazide and 3-hydroxy-N'-(1-methylethylidene)-2-naphthoic acid hydrazide described in JP-A No. 2000-190704, bismercapto-oxadiazole compounds described in JP-A No. 2006-328310, pyrithione salt compounds described in JP-A No. 2009-40898, and cobalt hydroxide compounds described in JP-A No. 2006-249361.

Of them, preferable are N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (manufactured by Degussa, "Si-69"), bis(3-triethoxysilylpropyl)disulfide (manufactured by Degussa, "Si-75"), 1,6-bis(N,N'-dibenzylthiocarbamoyldithio)-hexane (manufactured by Bayer, "KA9188"), hexamethylene bisthiosulfate disodium salt dihydrate, 1,3-biscitraconimidemethylbenzene (manufactured by Flexsys, "Perkalink 900"), and alkylphenol•sulfur chloride condensates such as "Tackirol (registered trademark) AP, V-200" manufactured by Taoka Chemical Co., Ltd., and the like. The use amount of these agents improving viscoelastic property is preferably in the range of 0.1 to 10 parts by mass with respect to 100 parts by mass of the rubber component.

In blending zinc oxide, blending in the step (A) is preferable, and in blending a vulcanization accelerator, blending in the step (B) is preferable.

It is also possible to blend and knead various compounding agents conventionally used in the field of rubber. Such compounding agents include, for example, antioxidants; oils; fatty acids such as stearic acid and the like; coumarone•indene resins such as a coumarone resin NG4 (softening point: 81 to 100° C.) manufactured by Nippon Steel Chemical Co., Ltd., Process Resin AC5 (softening point: 75° C.) manufactured by Kobe Oil Chemical Industrial Co., Ltd., and the like; terpene type resins such as terpene resins, terpene•phenol resins, aromatic modified terpene resins and the like; rosin derivatives such as "Nikanol (registered trademark) A70" (softening point: 70 to 90° C.) manufactured by Mitsubishi Gas Chemical Company, Inc., and the like; hydrogenated rosin derivatives; novolac type alkylphenol resins; resol type alkylphenol resins; C5 type petroleum resins; and liquid polybutadiene. These compounding agents can be blended by any of the step (A) and the step (B).

The above-described oil includes process oils, vegetable fats and oils and the like. The process oil includes paraffinic process oils, naphthenic process oils, aromatic process oils and the like.

The above-described antioxidant includes, for example, those described in "Rubber Industry Handbook <Fourth edition>", pp. 436 to 443 edited by The Society of Rubber Science and Technology, Japan. Of them, N-phenyl-N'-1,3-dimethylbutyl-p-phenylenediamine (6PPD), a reaction product of aniline and acetone (TMDQ), poly(2,2,4-trimethyl-1,2-)dihydroquinoline) (manufactured by Matsubara Sangyo, "Antioxidant FR"), synthetic waxes (paraffin waxes and the like) and vegetable waxes are preferably used.

It is also possible to blend and knead vulcanizing agents such as morpholine disulfide and the like conventionally used in the field of rubber. It is preferable that these are blended in the step (B).

Further, a peptizer and a retarder may be blended and kneaded, furthermore, general various rubber chemicals and softening agents and the like may be blended and kneaded if necessary.

As the retarder, exemplified are phthalic anhydride, benzoic acid, salicylic acid, N-nitrosodiphenylamine, N-(cyclohexylthio)-phthalimide (CTP), sulfonamide derivatives, diphenylurea, bis(tridecyl)pentaerythritol-diphosphite and the like, and N-(cyclohexylthio)-phthalimide (CTP) is preferably used.

Though the retarder may be blended and kneaded in the step (A), it is preferable to blend and knead the retarder in the step (B).

Though the use amount of the retarder is not particularly restricted, it is preferably in the rage of 0.01 to 1 part by weight, particularly preferably in the range of 0.05 to 0.5 parts by mass with respect to 100 parts by mass of a rubber component.

The temperature in the step (A) is preferably 200° C. or lower, more preferably 120 to 180° C. The temperature in the step (B) is preferably 60 to 120° C.

Next, a step (C) of thermally treating the kneaded mixture obtained in the step (B) will be explained.

The temperature in thermal treatment is preferably 120 to 180° C. Thermal treatment is usually conducted under normal pressure or increased pressure.

The process of the present invention usually contains a step of processing the kneaded mixture into particular condition, before subjecting the kneaded mixture obtained in the step (B) to thermal treatment in the step (C). The vulcanized rubber includes vulcanized rubbers obtained by subjecting the kneaded mixture processed into particular condition to thermal treatment in the step (C).

Here, "step of processing the kneaded mixture into particular condition" includes, for example, "step of coating the kneaded mixture on a steel cord", "step of coating the kneaded mixture on a carcass fiber cord", "step of processing the kneaded mixture into the shape of a member for tread" and the like in the field of rubber. Members such as belts, carcasses, inner liners, side walls, treads (cap tread or under tread) and the like obtained respectively by these steps are usually further molded into the shape of a tire together with other members by a method usually conducted in the field of tire, that is, via a step of incorporating the kneaded mixture into a tire, a green tire containing the kneaded mixture is obtained and subjected to thermal treatment in the step (C). Such thermal treatment is usually conducted under increased pressure. The vulcanized rubber includes vulcanized rubbers constituting the above-described members of the tire thus obtained.

As the rubber component in a rubber compounding suitable for tread members suitable for large tires of trucks, buses, light trucks, construction vehicles and the like, preferable is a natural rubber single body or a blend composed of natural rubber as the main component and SBR and/or BR. As the filler, a carbon black single body or a blend composed of silica as the main component and carbon black is preferably used. Further, it is preferable to use concurrently a viscoelasticity improving agent such as N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (Si-69), bis(3-triethoxysilylpropyl)disulfide (Si-75), 1,6-bis(N,N'-dibenzylthiocarbamoyldithio)-hexane (manufactured by Bayer, "KA9188"), hexamethylene bisthiosulfate disodium salt dihydrate, 1,3-biscitraconimidemethylbenzene (manufactured by Flexsys, "Perkalink 900"), alkylphenol•sulfur chloride condensates such as "Tackirol (registered trademark) AP, V-200" manufactured by Taoka Chemical Co., Ltd. and the like, etc.

As the rubber component in a rubber compounding suitable for tread members suitable for passenger car tires, preferable is a solution polymerized SBR single body having a molecular end modified with a silicon compound or a blend composed of the above-described end-modified solution polymerized SBR as the main component and at least one rubber selected from the group consisting of non-modified solution polymerized SBR, emulsion polymerized SBR, natural rubber and BR. As the filler, a blend composed of silica as the main component and carbon black is preferably used. Further, it is preferable to use concurrently a viscoelasticity improving agent such as N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (Si-69), bis(3-triethoxysilylpropyl)disulfide (Si-75), 1,6-bis(N,N'-dibenzylthiocarbamoyldithio)-hexane (manufactured by Bayer, "KA9188"), hexamethylene bisthiosulfate disodium salt dihydrate, 1,3-biscitraconimidemethylbenzene (manufactured by Flexsys, "Perkalink 900"), alkylphenol•sulfur chloride condensates such as "Tackirol (registered trademark) AP, V-200" manufactured by Taoka Chemical Co., Ltd. and the like, etc.

As the rubber component in a rubber compounding suitable for side wall members, preferable is a blend composed of BR as the main component and at least one rubber selected from the group consisting of non-modified solution polymerized SBR, emulsion polymerized SBR and natural rubber. As the filler, a carbon black single body or a blend composed of carbon black as the main component and silica is preferably used. Further, it is preferable to use concurrently a viscoelasticity improving agent such as N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (Si-69), bis(3-triethoxysilylpropyl)disulfide (Si-75), 1,6-bis(N,N'-dibenzylthiocarbamoyldithio)-hexane (manufactured by Bayer, "KA9188"), hexamethylene bisthiosulfate disodium salt dihydrate, 1,3-biscitraconimidemethylbenzene (manufactured by Flexsys, "Perkalink 900"), alkylphenol•sulfur chloride condensates such as "Tackirol (registered trademark) AP, V-200" manufactured by Taoka Chemical Co., Ltd. and the like, etc.

As the rubber component in a rubber compounding suitable for carcass and belt members, preferable is a natural rubber single body or a blend composed of natural rubber as the main component and BR. As the filler, a carbon black single body or a blend composed of carbon black as the main component and silica is preferably used. Further, it is preferable to use concurrently a viscoelasticity improving agent such as N,N'-bis(2-methyl-2-nitropropyl)-1,6-hexanediamine (manufactured by Sumitomo Chemical Co., Ltd., "Sumifine (registered trademark) 1162"), 5-nitroso-8-hydroxyquinoline (NQ-58), bis(3-triethoxysilylpropyl)tetrasulfide (Si-69), bis(3-triethoxysilylpropyl)disulfide (Si-75), 1,6-bis(N,N'-dibenzylthiocarbamoyldithio)-hexane (manufactured by Bayer, "KA9188"), hexamethylene bisthiosulfate disodium salt dihydrate, 1,3-biscitraconimidemethylbenzene (manufactured by Flexsys, "Perkalink 900"), alkylphenol. sulfur chloride condensates such as "Tackirol (registered trademark) AP, V-200" manufactured by Taoka Chemical Co., Ltd. and the like, etc.

Thus, vulcanized rubber is obtained. Fuel consumption of a car installed with a tire containing this vulcanized rubber is improved, and lowered fuel consumption can be obtained. This vulcanized rubber can be used not only for the above-described tire applications, but also used as vibration-proof rubber of car parts such as an engine mount, a strut mount, a bush, an exhaust hanger and the like. Such vibration-proof rubber for car is usually obtained by processing the kneaded mixture obtained in the step (B) into the shape of the above-described vibration-proof rubber for car, then, subjecting thermal treatment in the step (C).

The composition of the present invention contains particles of a compound represented by formula (I) (hereinafter, referred to as "compound (I)" in some cases) with a median diameter (50% D) of 100 μm or less (hereinafter, referred to as "atomized particles (I)" in some cases) and particles of at least one member selected from the group consisting of silica, talc and clay with a median diameter (50% D) of 100 μm or less (hereinafter, referred to as "atomized inorganic particle" in some cases).

Particles are arranged in ascending order from particles having smaller diameters, and the diameter of a particle at 50% on a volume basis is called "median diameter (50% D)". Particles are arranged in ascending order from particles having smaller diameters, and the diameter of a particle at 95% on a volume basis is called "95% particle diameter (95% D)".

The composition of the present invention can be obtained, for example, by pulverizing particles of a compound represented by formula (I) with a median diameter (50% D) of over 100 μm (hereinafter, referred to as "particle (I)" in some cases) by using a pulverizer in the presence of at least one member selected from the group consisting of silica, talc and clay (hereinafter, referred to as "inorganic particle" in some cases).

The method of pulverizing particles (I) by using a pulverizer in the presence of inorganic particles is the same as the process of the present invention described above.

Regarding the content ratio of atomized particles (I) and atomized inorganic particles in the composition, the amount of the atomized inorganic particles is preferably in the range of 0.01 to 19 parts by mass, more preferably in the range of 0.1 to 9 parts by mass, further preferably in the range of 0.4 to 4 parts by mass with respect to 1 part by mass of the atomized particles (I).

The at least one member selected from the group consisting of silica, talc and clay is the same as described above.

The compound (I) is the same as described above.

The median diameter (50% D) of atomized particles (I) is 100 μm or less, preferably 70 μm or less, more preferably 40 μm or less, further preferably less than 10 μm. The lower limit thereof is preferably 1 μm or more. The median diameter (50% D) can be measured by a laser diffraction method. When the median diameter is in the above-described range, the dispersibility of atomized particles (I) in vulcanized rubber is good, and the viscoelastic property of vulcanized rubber containing atomized particles (I) tends to be improved. The median diameter (50% D) of a mixture of atomized particles (I) and atomized inorganic particles is used as the median diameter (50% D) of atomized particles (I).

The 95% particle diameter (95% D) of atomized particles (I) is usually 150 μm or less, preferably 100 μm or less, more preferably 50 μm or less, further preferably 40 μm or less. The lower limit thereof is preferably 1 μm or more. The 95% particle diameter (95% D) can be measured by a laser diffraction method. When the 95% particle diameter is in the above-described range, the dispersibility of atomized particles (I) in vulcanized rubber is good, and the viscoelastic property of vulcanized rubber containing atomized particles (I) tends to be improved. The 95% particle diameter (95% D) of a mixture of atomized particles (I) and atomized inorganic particles is used as the 95% particle diameter (95% D) of atomized particles (I).

The median diameter (50% D) of atomized inorganic particles is 100 μm or less, preferably 70 μm or less, more preferably 40 μm or less, further preferably less than 10 μm. The median diameter (50% D) can be measured by a laser diffraction method. The median diameter (50% D) of a mixture of atomized particles (I) and atomized inorganic particles is used as the median diameter (50% D) of atomized inorganic particles.

The 95% particle diameter (95% D) of atomized inorganic particles is usually 150 μm or less, preferably 100 μm or less, more preferably 50 μm or less, further preferably 40 μm or less. The lower limit thereof is preferably 1 μm or more. The 95% particle diameter (95% D) can be measured by a laser diffraction method. The 95% particle diameter (95% D) of a mixture of atomized particles (I) and atomized inorganic particles is used as the 95% particle diameter (95% D) of atomized inorganic particles.

The composition of the present invention is compression-molded by a roll press machine and the like, to obtain lowered static bulk density and attain easy handling.

The rubber component and the like of a rubber composition obtained by kneading the composition of the present invention, a rubber component and a filler are the same as described above, and also the process thereof is the same as described above.

EXAMPLES

The present invention will be explained specifically using examples, test examples, production examples and the like listed below, but the present invention is not limited to them. Hereinafter, "parts" are by mass.

Production Example 1

Particle (I)

Into a nitrogen-purged reaction vessel were charged 100 parts (0.77 mol) of 3-chloropropylamine hydrochloride, 180 mL of water and 200.4 parts (0.81 mol) of sodium thiosulfate pentahydrate, and the resultant mixture was stirred at a bath temperature of 70 to 80° C. for 5 hours. The reaction mixture was allowed to cool overnight, the crystal was isolated by filtration, then, washed with water and methanol. The resultant crystal was dried at 50° C. for 4 hours, to obtain particles (I).

$^1$H-NMR (270.05 MHz, D$_2$O) $\delta_{ppm}$: 3.0-3.1 (4H, m), 2.0-2.1 (2H, m)

The median diameter (50% D) of the resultant particles (I) was measured by a laser diffraction method using type SALD-2000J manufactured by Shimadzu Corp., to find a value of 185 μm.

The 95% particle diameter (95% D) of the resultant particles (I) was measured by a laser diffraction method using type SALD-2000J manufactured by Shimadzu Corp., to find a value of 297 μm.

<Measuring Operation>

The resultant particles (I) were dispersed at room temperature into a mixed solution composed of toluene and a toluene solution of di-2-ethylhexyl sulfosuccinate sodium salt (concentration of di-2-ethylhexyl sulfosuccinate sodium salt: 10% by mass), and the resultant dispersion was stirred for 5 minutes while irradiating the dispersion with ultrasonic wave, to obtain a test solution. The test solution was transferred to a batch cell, and 1 minute after, the median diameter (50% D) and the 95% particle diameter (95% D) were measured. The refractive index was set at 1.70-0.20i in the measurement.

Example 1

The particles (I) obtained in Production Example 1 and silica gel (VN3, manufactured by Tosoh Silica Corporation) were mixed at a ratio of 1:3 (parts by mass). The resultant mixture was fed to a jet mill (pulverizer A) at a feeding rate of 10.7 kg/h (the feeding rate of the particles (I) obtained in Production Example 1 was 2.7 kg/h), to obtain a pulverized material. Adhesion of a powder to the inner part of the jet mill was not observed.

Pulverizer A: type PJM-200SP manufactured by Nippon Pneumatic Mfg Co., Ltd.

Compressed air feeding amount: 2.8 Nm$^3$/min

Pulverization pressure: 0.64 MPa

The median diameter (50% D) of the pulverized material obtained in Example 1 was measured by a laser diffraction method using type MT3300 manufactured by Nikkiso Co., Ltd., to find a value of 6.4 μm.

The 95% particle diameter (95% D) of the pulverized material obtained in Example 1 was measured by a laser diffraction method using type MT3300 manufactured by Nikkiso Co., Ltd., to find a value of 11.7 μm.

<Measuring Operation>

The resultant pulverized material was dispersed at room temperature into a mixed solution composed of isopropyl alcohol and an isopropyl alcohol solution of di-2-ethylhexyl sulfosuccinate sodium salt (concentration of di-2-ethylhexyl sulfosuccinate sodium salt: 10% by mass), and the resultant dispersion was stirred for 5 minutes while irradiating the dispersion with ultrasonic wave, to obtain a test solution. The test solution was transferred to a batch cell, and 1 minute after, the median diameter (50% D) and the 95% particle diameter (95% D) were measured. The refractive index was set at 1.70-0.20i in the measurement.

The median diameter (50% D) and the like were measured according to Example 1 under conditions shown in the following table.

TABLE 1

| | Particle (I) (parts)/inorganic particle (parts) | Kind of inorganic particle | Kind of pulverizer |
|---|---|---|---|
| Example 1 | 1/3 | VN3 | A |
| Example 2 | 1/1 | VN3 | A |
| Example 3 | 1/0.3 | VN3 | A |
| Example 4 | 1/3 | VN3 | A |
| Example 5 | 1/3 | AQ | A |
| Example 6 | 1/3 | AQ | A |
| Example 7 | 1/1 | AQ | B |
| Example 8 | 1/1 | AQ | C |
| Example 9 | 1/9 | AQ | C |
| Example 10 | 1/3 | AQ | C |
| Example 11 | 1/0.4 | AQ | C |
| Example 12 | 1/0.3 | AQ | C |
| Example 13 | 1/0.1 | AQ | C |
| Example 14 | 1/1 | VN3 | C |
| Example 15 | 1/3 | VN3 | C |
| Reference Example 1 | 1/0 | — | A |
| Reference Example 2 | 0/1 | AQ | C |
| Reference Example 3 | 0/1 | VN3 | C |

| | Feeding rate of mixture (feeding rate of particle (I)) (kg/h) | Evaluation of powder adhesion |
|---|---|---|
| Example 1 | 10.7 (2.7) | A |
| Example 2 | 9.1 (4.6) | B |
| Example 3 | 9.8 (6.5) | B |
| Example 4 | 7.7 (1.9) | A |
| Example 5 | 10.1 (2.5) | A |
| Example 6 | 5.7 (1.4) | A |
| Example 7 | 1.2 (0.6) | A |
| Example 8 | 0.016 (0.008) | A |
| Example 9 | 0.036 (0.004) | A |
| Example 10 | 0.014 (0.004) | A |
| Example 11 | 0.005 (0.004) | A |
| Example 12 | 0.005 (0.004) | B |
| Example 13 | 0.004 (0.004) | B |
| Example 14 | 0.007 (0.004) | A |
| Example 15 | 0.014 (0.004) | A |
| Reference Example 1 | 7.1 (7.1) | C |
| Reference Example 2 | 0.004 (—) | A |
| Reference Example 3 | 0.004 (—) | A |

TABLE 1-continued

Example 3

| | Median diameter (μm) | 95% particle diameter (μm) |
|---|---|---|
| Example 1 | 6.4 | 11.7 |
| Example 2 | 6.6 | 17.7 |
| Example 3 | 8.4 | 25.6 |
| Example 4 | 6.1 | 16.7 |
| Example 5 | 6.9 | 18.0 |
| Example 6 | 4.8 | 12.3 |
| Example 7 | 6.5 | 19.7 |
| Example 8 | 9.7 | 26.8 |
| Example 9 | 8.5 | 25.1 |
| Example 10 | 9.2 | 25.0 |
| Example 11 | 8.5 | 22.2 |
| Example 12 | 9.1 | 25.5 |
| Example 13 | 9.4 | 26.3 |
| Example 14 | 9.1 | 23.5 |
| Example 15 | 9.7 | 27.5 |
| Reference Example 1 | 18.1 | 67.6 |
| Reference Example 2 | 5.2 | 8.0 |
| Reference Example 3 | 4.1 | 7.8 |

<Kind of inorganic particle>
VN3: manufactured by Tosoh Silica Corporation, VN3
AQ: manufactured by Tosoh Silica Corporation, AQ The median diameter (50% D) of silica gel VN3 was measured according to the measuring method and the measuring operation described in Production Example 1, to find a value of 31.8 μm.

The median diameter (50% D) of silica gel AQ was measured according to the measuring method and the measuring operation described in Production Example 1, to find a value of 34.7 μm.

<Kind of Pulverizer>
A: manufactured by Nippon Pneumatic Mfg Co., Ltd., type PJM-200SP
  Compressed air feeding amount: 2.8 Nm³/min
  Pulverization pressure: 0.64 MPa
B: manufactured by Nippon Pneumatic Mfg Co., Ltd., type PJM-80SP
  Compressed air feeding amount: 0.5 Nm³/min
  Pulverization pressure: 0.64 MPa
C: manufactured by Seishin Enterprise Co., Ltd., type A-O jet mill
  Compressed air feeding amount: 0.12 Nm³/min
  Pulverization pressure: 0.65 MPa <Evaluation of Powder Adhesion>
A: Adhesion of a powder to the inner part of the jet mill was not observed.
B: Adhesion of a powder to the inner part of the jet mill was slightly observed, however, continuous operation was possible.
C: Adhesion of a powder to the inner part of the jet mill was observed.

<Compression>
The pulverized materials obtained in Example 1 to 15 were compressed by a roll press machine. The static bulk density was measured, to find values of 0.1130 g/ml to 1.1400 g/ml.
Roll press machine: manufactured by Seishin Enterprise Co., Ltd., type RP-300
  Roll diameter×width: φ300 mm×300 mm
  Feeding rate: 1.5 to 2.5 kg/hr Example 16

The particles (I) obtained in the same manner as in Production Example 1 and talc (manufactured by Nippon Talc Co., Ltd., MS-P) were mixed at a ratio of 25:75 (parts by mass). The resultant mixture was fed to a jet mill (pulverizer D) at a feeding rate of 1.1 kg/h, to obtain a pulverized material. Adhesion of a powder to the inner part of the jet mill was not observed. The median diameter (50% D) and the like were measured in the same manner as in Example 1, to find a value of 7.7 μm.

Pulverizer D: manufactured by Seishin Enterprise Co., Ltd., type CO-JET (mill material; alumina)

Feeding air pressure: 0.7 MPa

Air flow rate: 0.4 Nm³/min

Pulverization pressure: 0.7 MPa

Feeding rate: 1.1 kg/h

The median diameter (50% D) and the like were measured according to Example 16 under conditions show in the following table.

TABLE 2

| | Particle (I)/silica/talc/clay (parts) | Evaluation of powder adhesion |
|---|---|---|
| Example 16 | 25/0/75/0 | A |
| Example 17 | 25/0/0/75 | A |
| Example 18 | 25/50/25/0 | A |
| Example 19 | 25/25/25/25 | A |
| Example 20 | 25/0/50/25 | A |
| Example 21 | 25/50/0/25 | A |
| Reference Example 4 | 100/0/0/0 | C |

| | Median diameter (μm) | 95% particle diameter (μm) |
|---|---|---|
| Example 16 | 7.7 | 22.9 |
| Example 17 | 9.2 | 33.8 |
| Example 18 | 7.1 | 24.8 |
| Example 19 | 8.7 | 32.1 |
| Example 20 | 8.5 | 26.9 |
| Example 21 | 6.7 | 26.6 |
| Reference Example 4 | 27.9 | 114.0 |

<Inorganic particle>
Silica: manufactured by Tosoh Silica Corporation, Nipsil AQ
Talc: manufactured by Nippon Talc Co., Ltd., MS-P
Clay: manufactured by Agglochemiteck Corp., ST-KE Example 22

The particles (I) obtained in the same manner as in Production Example 1 and silica (manufactured by Tosoh Silica Corporation, AQ) were mixed at a ratio of 9:1 (parts by mass). The resultant mixture was fed to a hammer mill (pulverizer E), to obtain a pulverized material. Adhesion of a powder to the inner part of the hammer mill was not observed. The median diameter (50% D) and the like were measured in the same manner as in Example 1

Pulverizer E: manufactured by Hosokawa Micron Corporation, ACM Pulverizer

Model: ACM-15H

Pulverization rotor rotation frequency: 7800 rpm

Classification rotor rotation frequency: 7000 rpm

Air flow rate: 10 m³/min

The median diameter (50% D) and the like were measured according to Example 22 under conditions show in the following table.

TABLE 3

| | Particle (I)/silica (parts) | Classification rotor rotation direction |
|---|---|---|
| Example 22 | 9/1 | reverse direction |
| Example 23 | 9/1 | forward direction |
| Example 24 | 9/1 | forward direction |
| Reference Example 5 | 10/0 | forward direction |

| | Feeding rate (kg/h) | Pulverization frequency (number of rotation) |
|---|---|---|
| Example 22 | 18 | 1 |
| Example 23 | 29 | 1 |
| Example 24 | 12 | 2 |
| Reference Example 5 | 15 | 1 |

| | Evaluation of powder adhesion | Median diameter (μm) | 95% particle diameter (μm) |
|---|---|---|---|
| Example 22 | A | 29.5 | 96.1 |
| Example 23 | A | 31.1 | 104.0 |
| Example 24 | A | 27.1 | 80.4 |
| Reference Example 5 | C | 25.4 | 80.2 |

Example 25

The particles (I) obtained in the same manner as in Production Example 1 and silica (manufactured by Tosoh Silica Corporation, AQ) were mixed at a ratio of 9:1 (parts by mass). The resultant mixture was fed to a dry bead mill (pulverizer F), to obtain a pulverized material. Adhesion of a powder to the inner part of the bead mill was not observed. The median diameter (50% D) and the like were measured in the same manner as in Example 1

Pulverizer F: manufactured by Hosokawa Micron Corporation, Pulvis
  Model: type PV-250
  Pulverization rotor rotation frequency: 7800 rpm
  Classification rotor rotation frequency: 7000 rpm
  Air flow rate: 10 m³/min The median diameter (50% D) and the like were measured according to Example 25 under conditions show in the following table.

TABLE 4

| | Particle (I)/silica (parts) | Air flow rate (m³/min) | Classification rotor rotation frequency (×1000 rpm) |
|---|---|---|---|
| Example 25 | 9/1 | 0.6 | 10 |
| Example 26 | 9/1 | 0.6 | 10 |
| Example 27 | 9/1 | 0.6 | 5 |
| Reference Example 6 | 10/0 | 0.6 | 5 |

| | Feeding rate (kg/h) | Evaluation of powder adhesion | Median diameter (μm) | 95% Particle diameter (μm) |
|---|---|---|---|---|
| Example 25 | 0.2 | A | 6 | 11 |
| Example 26 | 0.4 | A | 5 | 8 |
| Example 27 | 1.0 | A | 7 | 13 |
| Reference Example 6 | 0.17 | C | 34 | 139 |

Example 28

The particles (I) obtained in Production Example 1 and silica (manufactured by Tosoh Silica Corporation, AQ) were mixed at a ratio of 9:1 (parts by mass). The resultant mixture was fed to a turbo mill (pulverizer G), to obtain a pulverized material. Adhesion of a powder to the inner part of the turbo mill was not observed. The median diameter (50% D) and the like were measured in the same manner as in Example 1

Pulverizer G: manufactured by Freund Turbo Corporation, turbo mill
  Model: T250
  Rotation frequency: 9600 rpm
  Classification rotor rotation frequency: 7000 rpm
  Air flow rate: 10 m³/min The median diameter (50% D) and the like were measured according to Example 28 under conditions show in the following table.

TABLE 5

| | Particle (I)/silica (parts) | Feeding rate (kg/h) | Pulverization frequency (number of rotation) |
|---|---|---|---|
| Example 28 | 9/1 | 27 | 1 |
| Example 29 | 9/1 | 34 | 2 |

| | Evaluation of powder adhesion | Median diameter (μm) | 95% particle diameter (μm) |
|---|---|---|---|
| Example 28 | B | 29.5 | 90.4 |
| Example 29 | B | 25.1 | 76.1 |

Example 30

<Step (A)>

Using a Banbury mixer (600 ml Laboplastomill manufactured by Toyo Seiki Seisaku-Sho Ltd.), 100 parts by mass of natural rubber (RSS #1), 45 parts by mass of HAF (manufactured by Asahi Carbon Co., Ltd., trade name "Asahi #70"), 3 parts by mass of stearic acid, 5 parts by mass of zinc oxide, 1 part by mass of an antioxidant (N-phenyl-N'-1,3-dimethylbutyl-p-phenylenediamine (6PPD): trade name "Antigen (registered trademark) 6C" manufactured by Sumitomo Chemical Co., Ltd.) and 2 parts by mass of the pulverized material obtained in Example 5 were kneaded, to obtain a kneaded mixture. In this step, various chemicals and fillers were charged, then, kneading was performed for 5 minutes at a mixer set temperature of 120° C. and a mixer rotation frequency of 50 rpm. The temperature of the kneaded mixture in completion of kneading was 168° C.

<Step (B)>

The kneaded mixture obtained in the step (A), 1 part by mass of a vulcanization accelerator N-cyclohexyl-2-benzothiazolesulfenamide (CBS) and 2 parts by mass of sulfur were blended by kneading in an open roll machine at a roll set temperature of 60° C., to obtain an unvulcanized rubber composition.

<Step (C)>

The unvulcanized rubber composition obtained in the step (B) was thermally treated at 145° C., to obtain vulcanized rubber.

Reference Example 7

An unvulcanized rubber composition and vulcanized rubber were obtained in the same manner as in Example 30 excepting that the pulverized material obtained in Example 5 was not used in Example 30. The temperature after completion of kneading of the step (A) was 163° C.

Test Example 1

The dispersibility of the compound (I) of the unvulcanized rubber composition obtained in the step (B) of Example 30, and the viscoelastic property of the vulcanized rubber obtained in the step (C) were measured as described below.
(1) Dispersibility of Compound (I)
An unvulcanized rubber composition was sheeted, and the cross-section thereof was observed visually, and the presence or absence of an un-dissolved material of a compound (1) was determined.
(2) Dynamic Viscoelastic Property (Tan δ)
It was measured using a viscoelasticity analyzer manufactured by Ueshima Seisakusho Co., Ltd.
Conditions: temperature 60° C., initial strain 10%, dynamic strain 2.5%, frequency 10 Hz In the unvulcanized rubber composition obtained in the step (B) of Example 30, an unmelted material of a compound (I) was not recognized, and dispersibility was excellent. When the vulcanized rubber obtained in Reference Example 7 was used as control, the vulcanized rubber obtained in Example 30 showed a decrease in the dynamic viscoelastic property (tan δ at 60° C.) of 22%, and an improvement in the physical property was confirmed.

Example 31

Vulcanized rubber was obtained in the same manner as in Example 30 excepting that 1 part by mass of the pulverized material obtained in Example 7 was used instead of 2 parts by mass of the pulverized material obtained in Example 5, in Example 30. The temperature after completion of kneading of the step (A) was 167° C.

Test Example 2

The same measurement as in Test Example 1 was conducted for the unvulcanized rubber composition obtained in Example 31, an unmelted material of a compound (I) was not recognized, and dispersibility was excellent. When the vulcanized rubber obtained in Reference Example was used as control, the rubber obtained in Example 31 showed a decrease in the dynamic viscoelastic property (tan δ at 60° C.) of 27%, and an improvement in the physical property was confirmed.

Comparative Reference Example 1

Vulcanized rubber was obtained in the same manner as in Example 30 excepting that 0.5 parts by mass of a compound (I) having a median diameter (50% D) of 29 μm was used instead of 2 parts by mass of the pulverized material obtained in Example 5, in Example 30. The temperature after completion of kneading of the step (A) was 165° C.

Comparative Test Example 1

The same measurement as in Test Example 1 was conducted for the unvulcanized rubber composition obtained in Comparative Reference Example 1, an unmelted material of a compound (I) was not recognized, and dispersibility was excellent. When the vulcanized rubber obtained in Reference Example was used as control, the rubber obtained in Comparative Reference Example showed a decrease in the dynamic viscoelastic property (tan δ at 60° C.) of 19%, and an improvement in the physical property was confirmed. However, the improvement in the viscoelastic property of the vulcanized rubber was somewhat insufficient, in comparison with Examples 30 and 31.

Comparative Reference Example 2

Vulcanized rubber was obtained in the same manner as in Example 30 excepting that 0.5 parts by mass of a compound (I) obtained in Production Example 1 having a median diameter (50% D) of 185 μm was used instead of 2 parts by mass of the pulverized material obtained in Example 5, in Example 30. The temperature after completion of kneading of the step (A) was 162° C.

Comparative Test Example 2

The same measurement as in Test Example 1 was conducted for the unvulcanized rubber composition obtained in Comparative Reference Example 2, an unmelted material of a compound (I) was recognized, and dispersibility was poor. When the vulcanized rubber obtained in Reference Example was used as control, the rubber obtained in Comparative Test Example 2 showed a decrease in the dynamic viscoelastic property (tan δ at 60° C.) of only 10%, and the improvement in the viscoelastic property of the vulcanized rubber was insufficient, in comparison with Examples 30 and 31.

Example 32

When a steel cord treated by brass plating is coated with the kneaded mixture obtained in the step (B) of Examples 30 and 31, a belt is obtained. Using the resulting belt, a green tire is molded according to a usual production method, and the resultant green tire is heated and pressed in a vulcanizer, to obtain a vulcanized tire.

Example 33

The kneaded mixture obtained in the step (B) of Examples 30 and 31 is extrusion-processed, to obtain a member for tread. Using the resulting member for tread, a green tire is molded according to a usual production method, and the resultant green tire is heated and pressed in a vulcanizer, to obtain a vulcanized tire.

Example 34

The kneaded mixture obtained in the step (B) of Examples 30 and 31 is extrusion-processed, to prepare a kneaded mixture having a shape corresponding to the shape of a carcass, and the kneaded mixture is pasted on the upper and lower sides of a carcass fiber cord made of polyester, to obtain a carcass. Using the resulting carcass, a green tire is molded according to a usual production method, and the resultant green tire is heated and pressed in a vulcanizer, to obtain a vulcanized tire.

Example 35

The vulcanized rubber obtained by the following steps (A) to (C) is suitable for a cap tread.
<Step (A)>
Using a Banbury mixer (600 ml Laboplastomill manufactured by Toyo Seiki Seisaku-Sho Ltd.), 100 parts by mass of styrene-butadiene copolymerized rubber SBR #1502 (manufactured by Sumitomo Chemical Co., Ltd.), 45 parts by mass of ISAF-HM (manufactured by Asahi Carbon Co., Ltd., trade name "Asahi #80"), 2 parts by mass of stearic acid, 3 parts by mass of zinc oxide, 4 parts by mass of the pulverized material obtained in Example 5, 1 part by mass of an antioxidant (N-phenyl-N'-1,3-dimethylbutyl-p-phenylenediamine (6PPD): trade name "Antigen (registered trademark) 6C" manufactured by Sumitomo Chemical Co., Ltd.) and 2 parts by mass of a wax ("OZOACE-0355" manufactured by Nippon Seiro Co., Ltd.) were blended by kneading, to obtain a rubber composition. In this step, various chemicals and fillers were charged, then, kneaded at a mixer rotation frequency of 50 rpm for 5 minutes, and the rubber temperature in this procedure was 160 to 175° C.
<Step (B)>
The rubber composition obtained in the step (A), 3 parts by mass of a vulcanization accelerator N-cyclohexyl-2-benzothiazolesulfenamide (CBS) and 2 parts by mass of sulfur were blended by kneading in an open roll machine at a temperature of 60 to 80° C., to obtain a kneaded mixture.
<Step (C)>
The kneaded mixture obtained in the step (B) was thermally treated at 145° C. to obtain vulcanized rubber.

Example 36

The vulcanized rubber obtained by the following steps (A) to (C) is suitable for an under tread.
<Step (A)>
Using a Banbury mixer (600 ml Laboplastomill manufactured by Toyo Seiki Seisaku-Sho Ltd.), 100 parts by mass of styrene-butadiene copolymerized rubber SBR #1502 (manufactured by Sumitomo Chemical Co., Ltd.), 35 parts by mass of ISAF-HM (manufactured by Asahi Carbon Co., Ltd., trade name "Asahi #80"), 2 parts by mass of stearic acid, 3 parts by mass of zinc oxide, 4 parts by mass of the pulverized material obtained in Example 5, 1 part by mass an antioxidant (N-phenyl-N'-1,3-dimethylbutyl-p-phenylenediamine (6PPD): trade name "Antigen (registered trademark) 6C" manufactured by Sumitomo Chemical Co., Ltd.) and 2 parts by mass a wax ("OZOACE-0355" manufactured by Nippon Seiro Co., Ltd.) were blended by kneading, to obtain a rubber composition. In this step, various chemicals and fillers were charged, then, kneaded at a mixer rotation frequency of 50 rpm for 5 minutes, and the rubber temperature in this procedure was 160 to 175° C.
<Step (B)>
The rubber composition obtained in the step (A), 2 parts by mass of a vulcanization accelerator N-cyclohexyl-2-benzothiazolesulfenamide (CBS), 0.5 parts by mass of a vulcanization accelerator diphenylguanidine (DPG), 0.8 parts by mass of a vulcanization accelerator dibenzothiazyl disulfide (MBTS) and 1 part by mass of sulfur were blended by kneading in an open roll machine at a temperature of 60 to 80° C., to obtain a kneaded mixture.
<Step (C)>
The kneaded mixture obtained in the step (B) was thermally treated at 145° C. to obtain vulcanized rubber.

Example 37

The vulcanized rubber obtained by the following steps (A) to (C) is suitable for a belt.
<Step (A)>
Using a Banbury mixer (600 ml Laboplastomill manufactured by Toyo Seiki Seisaku-Sho Ltd.), 100 parts by mass of natural rubber (RSS #1), 45 parts by mass of HAF (manufactured by Asahi Carbon Co., Ltd., trade name "Asahi #70"), 3 parts by mass of stearic acid, 5 parts by mass of zinc oxide, 4 parts by mass of the pulverized material obtained in Example 5, 10 parts by mass of hydrous silica (manufactured by Tosoh Silica Corporation, "Nipsil (registered trademark) AQ", 2 parts by mass of an antioxidant FR (manufactured by Matsubara Sangyo "Antioxidant FR"), 2 parts by mass of resorcin and 2 parts by mass of cobalt naphthenate were blended by kneading, to obtain a rubber composition. In this step, various chemicals and fillers were charged, then, kneaded at a mixer rotation frequency of 50 rpm for 5 minutes, and the rubber temperature in this procedure was 160 to 175° C.
<Step (B)>
The rubber composition obtained in the step (A), 1 part by mass of a vulcanization accelerator N,N-dicyclohexyl-2-benzothiazolesulfenamide (DCBS), 6 parts by mass of sulfur and 3 parts by mass of methoxylated methylolmelamine resin ("Sumikanol 507AP" manufactured by Sumitomo Chemical Co., Ltd.) were blended by kneading in an open roll machine at a temperature of 60 to 80° C., to obtain a kneaded mixture.
<Step (C)>
The kneaded mixture obtained in the step (B) was thermally treated at 145° C. to obtain vulcanized rubber.

Example 38

The vulcanized rubber obtained by the following steps (A) to (C) is suitable for an inner liner.
<Step (A)>
Using a Banbury mixer (600 ml Laboplastomill manufactured by Toyo Seiki Seisaku-Sho Ltd.), 100 parts by mass of halogenated butyl rubber ("Br-IIR2255" manufactured by Exxon Mobil Corporation), 60 parts by mass of GPF, 1 part by mass of stearic acid, 3 parts by mass of zinc oxide, 4 parts by mass of the pulverized material obtained in Example 5 and 10 parts by mass of a paraffin oil ("Diana Process Oil" manufactured by Idemitsu Kosan Co., Ltd.) were blended by kneading, to obtain a rubber composition. In this step, various chemicals and fillers were charged, then, kneaded at a mixer rotation frequency of 50 rpm for 5 minutes, and the rubber temperature in this procedure was 160 to 175° C.
<Step (B)>
The rubber composition obtained in the step (A), 1 part by mass of an antioxidant (condensate of aniline and acetone (TMDQ)), 1 part by mass of a vulcanization accelerator dibenzothiazyl disulfide (MBTS) and 2 parts by mass of sulfur were blended by kneading in an open roll machine at a temperature of 60 to 80° C., to obtain a kneaded mixture.
<Step (C)>
The kneaded mixture obtained in the step (B) was thermally treated at 145° C. to obtain vulcanized rubber.

Example 39

The vulcanized rubber obtained by the following steps (A) to (C) is suitable for a side wall.
<Step (A)>
Using a Banbury mixer (600 ml Laboplastomill manufactured by Toyo Seiki Seisaku-Sho Ltd.), 40 parts by mass of natural rubber (RSS #3), 60 parts of polybutadiene rubber ("BR150B" manufactured by Ube Industries, Ltd.), 50 parts by mass of FEF, 2.5 parts by mass of stearic acid, 3 parts by mass of zinc oxide, 4 parts by mass of the pulverized material obtained in Example 5, 2 parts by mass of an antioxidant (N-phenyl-N'-1,3-dimethylbutyl-p-phenylenediamine (6PPD): trade name "Antigen (registered trademark) 6C" manufactured by Sumitomo Chemical Co., Ltd.), 10 parts by mass of an aromatic oil ("NC-140" manufactured by COSMO Oil Co., Ltd.) and 2 parts by mass of a wax ("Sunnock (registered trademark) wax" manufactured by Ouchi Shinko Chemical Industrial Co., Ltd.) were blended by kneading, to obtain a rubber composition. In this step, various chemicals and fillers were charged, then, kneaded at a mixer rotation frequency of 50 rpm for 5 minutes, and the rubber temperature in this procedure was 160 to 175° C.
<Step (B)>
The rubber composition obtained in the step (A), 0.75 parts by mass of a vulcanization accelerator N-tert-butyl-2-benzothiazolylsulfenamide (BBS) and 1.5 parts by mass of sulfur were blended by kneading in an open roll machine at a temperature of 60 to 80° C., to obtain a kneaded mixture.
<Step (C)>
The kneaded mixture obtained in the step (B) was thermally treated at 145° C. to obtain vulcanized rubber.

Example 40

The vulcanized rubber obtained by the following steps (A) to (C) is suitable for a carcass.
<Step (A)>
Using a Banbury mixer (600 ml Laboplastomill manufactured by Toyo Seiki Seisaku-Sho Ltd.), 70 parts by mass of natural rubber (TSR20), 30 parts by mass of styrene-butadiene copolymerized rubber SBR #1502 (manufactured by Sumitomo Chemical Co., Ltd.), 60 parts by mass of N339 (manufactured by Mitsubishi Chemical Corporation), 2 parts by mass of stearic acid, 5 parts by mass of zinc oxide, 7 parts by mass of a process oil ("Diana Process PS32" manufactured by Idemitsu Kosan Co., Ltd.) and 4 parts by mass of the pulverized material obtained in Example 5 were blended by kneading, to obtain a rubber composition. In this step, various chemicals and fillers were charged, then, kneaded at a mixer rotation frequency of 50 rpm for 5 minutes, and the rubber temperature in this procedure was 160 to 175° C.
<Step (B)>
The rubber composition obtained in the step (A), 1 part by mass of a vulcanization accelerator N-tert-butyl-2-benzothiazolylsulfenamide (BBS), 3 parts by mass of sulfur, 1 part by mass of an antioxidant (N-phenyl-N'-1,3-dimethylbutyl-p-phenylenediamine (6PPD): trade name "Antigen (registered trademark) 6C" manufactured by Sumitomo Chemical Co., Ltd.) and 1 part by mass of an antioxidant (condensate of aniline and acetone (TMDQ)) were blended by kneading in an open roll machine at a temperature of 60 to 80° C., to obtain a kneaded mixture.
<Step (C)>
The kneaded mixture obtained in the step (B) was thermally treated at 145° C. to obtain vulcanized rubber.

Example 41

The vulcanized rubber obtained by the following steps (A) to (C) is suitable for a cap tread.
<Step (A)>
Using a Banbury mixer (600 ml Laboplastomill manufactured by Toyo Seiki Seisaku-Sho Ltd.), 100 parts by mass of styrene-butadiene copolymerized rubber SBR #1500 (manufactured by JSR), 78.4 parts by mass of silica (trade name: "Ultrasil (registered trademark) VN3-G" manufactured by Degussa), 6.4 parts by mass of carbon black (trade name: "N-339" manufactured by Mitsubishi Chemical Corporation), 6.4 parts by mass of a silane coupling agent (bis(3-triethoxysilylpropyl)tetrasulfide: trade name "Si-69" manufactured by Degussa), 47.6 parts by mass of a process oil (trade name: "NC-140" manufactured by COSMO Oil Co., Ltd.), 1.5 parts by mass of an antioxidant (N-phenyl-N'-1,3-dimethylbutyl-p-phenylenediamine (6PPD), trade name: "Antigen (registered trademark) 6C" manufactured by Sumitomo Chemical Co., Ltd.), 2 parts by mass of zinc oxide, 2 parts by mass of stearic acid and 12 parts by mass of the pulverized material obtained in Example 5 were blended by kneading, to obtain a rubber composition. In this step, the operation was conducted at a temperature in the range of 70° C. to 120° C., various chemicals and fillers were charged, then, kneaded at a mixer rotation frequency of 80 rpm for 5 minutes, and subsequently, kneaded at a mixer rotation frequency of 100 rpm for 5 minutes.
<Step (B)>
The rubber composition obtained in the step (A), 1 part by mass a vulcanization accelerator N-cyclohexyl-2-benzothiazolesulfenamide (CBS), 1 part by mass of a vulcanization accelerator diphenylguanidine (DPG), 1.5 parts by mass of a wax (trade name: "Sunnock (registered trademark) N" manufactured by Ouchi Shinko Chemical Industrial Co., Ltd.) and 1.4 parts by mass of sulfur were blended by kneading in an open roll machine at a temperature of 30 to 80° C., to obtain a kneaded mixture.
<Step (C)>
The kneaded mixture obtained in the step (B) was thermally treated at 160° C., to obtain vulcanized rubber.

Example 42

Vulcanized rubber was obtained in the same manner as in Example 41 excepting that solution polymerized SBR ("Asaprene (registered trademark)" manufactured by Asahi Kasei Chemicals Corporation) was used instead of the styrene-butadiene copolymerized rubber SBR #1500 (manufactured by JSR), in Example 41. This vulcanized rubber is suitable for a cap tread.

Example 43

Vulcanized rubber was obtained in the same manner as in Example 41 excepting that SBR #1712 (manufactured by JSR) was used instead of the styene-butadiene copolymerized rubber SBR #1500 (manufactured by JSR), the use amount of the process oil was changed to 21 parts by mass, and the timing of charging of zinc oxide was changed to the second step, in Example 41. This vulcanized rubber is suitable for a cap tread.

INDUSTRIAL APPLICABILITY

According to the present invention, atomized particles of a compound represented by formula (I) can be obtained easily.

The invention claimed is:
1. A process for producing particles, the process comprising pulverizing particles of a compound represented by formula (I) with a median diameter (50% D) of over 100 μm by using a pulverizer in the presence of at least one member selected from the group consisting of silica, talc and clay, to obtain particles of the compound represented by formula (I) with a median diameter (50% D) of 100 μm or less,

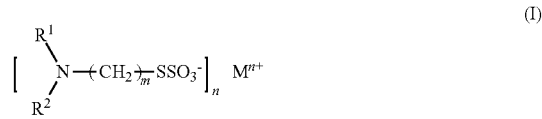

in formula (I), $R^1$ and $R^2$ each independently represent a hydrogen atom or an alkyl group having 1 to 6 carbon atoms, or alternatively, $R^1$ and $R^2$ are linked to each other to form a ring together with the nitrogen atom to which they are bound, m represents an integer of 2 to 9, $M^{n+}$ represents $H^+$ or an n-valent metal ion, and n represents an integer of 1 or 2.

2. The process according to claim 1, wherein the compound represented by formula (I) is a compound represented by formula (I-1):

(I-1)

3. The process according to claim 1, wherein the pulverization is performed in the presence of at least one member selected from the group consisting of silica, talc and clay in an amount of 0.1 to 9 parts by mass with respect to 1 part by mass of the compound represented by formula (I).

4. The process according to claim 1, wherein particles of a compound represented by formula (I) with a median diameter (50% D) of less than 10 μm are obtained.

5. The process according to claim 1, wherein the pulverizer is a jet mill or a bead mill.

6. The process according to claim 1, wherein the particles of a compound represented by formula (I) with a median diameter (50% D) of 100 μm or less are particles of a compound represented by formula (I) with a 95% particle diameter (95% D) of 50 μm or less.

7. A process for producing vulcanized rubber, the process comprising step (A) of kneading particles obtained by the process according to claim 1, a rubber component and a filler together, step (B) of kneading the kneaded mixture obtained in the step (A), a sulfur component and a vulcanization accelerator, and step (C) of thermally treating the kneaded mixture obtained in the step (B).

* * * * *